United States Patent
Simons et al.

(10) Patent No.: US 7,202,212 B2
(45) Date of Patent: Apr. 10, 2007

(54) METHOD FOR PR-39 PEPTIDE MEDIATED SELECTIVE INHIBITION OF IκBα DEGRADATION

(75) Inventors: Michael Simons, Chestnut Hill, MA (US); Youhe Gao, Brighton, MA (US)

(73) Assignee: Beth Israel Deaconess Medical Center, Boston, MA (US)

( * ) Notice: Subject to any disclaimer, the term of this patent is extended or adjusted under 35 U.S.C. 154(b) by 473 days.

(21) Appl. No.: 10/391,155

(22) Filed: Mar. 18, 2003

(65) Prior Publication Data

US 2004/0009463 A1    Jan. 15, 2004

Related U.S. Application Data

(63) Continuation-in-part of application No. 09/276,868, filed on Mar. 26, 1999, and a continuation-in-part of application No. 09/426,011, filed on Oct. 25, 1999.

(51) Int. Cl.
*C12N 5/00* (2006.01)

(52) U.S. Cl. ............... 514/12; 514/2; 514/15; 435/1.1; 435/4; 435/325

(58) Field of Classification Search ............ 514/2, 514/12, 15; 435/325, 4, 1.1
See application file for complete search history.

(56) References Cited

OTHER PUBLICATIONS

Anderson. Nature vol. 392. 1998. pp. 25-30.*
Verma et al. Nature vol. 389. 1997. pp. 239-242.*

\* cited by examiner

*Primary Examiner*—Leon B. Lankford, Jr.
(74) *Attorney, Agent, or Firm*—David Prashker, Esq.

(57) ABSTRACT

The present invention provides both a method and means for regulating IκBα degradation, NFκB activity, and NFκB-dependent gene expression within living cells, tissues, and organs in-situ. The selective regulation is performed using native PR-39 peptide or one of its shorter-length homologs, for interaction with such IκBα and proteasomes as are present in the cytoplasm of viable cells. The result of PR-39 peptide interaction with IκBα is a selective alteration in the intracellular proteolytic activity of proteasomes, which in turn, causes a reduction of IκBα, a decrease of NFκB activity, and a down-regulation of NFκB-dependent gene expression.

7 Claims, 8 Drawing Sheets

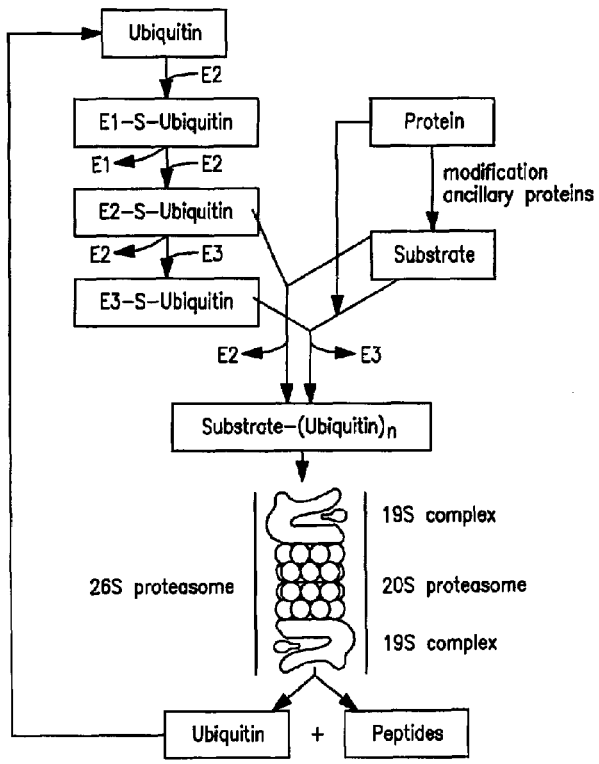

*Schematic representation of the proteasome-ubiquitin pathway. Ubiquitin is first activated by a ubiquitin-activating enzyme (UBA or E1) and passed on to a ubiquitin-conjugating protein (UBC or E2). Ubiquitin is then linked directly, or with the help of ubiquitin ligases (E3), via an isopeptide bond to a lysine residue of the substrate protein. Polyubiquititinated proteins are recognized and selectively degraded by the 26S proteasome, yielding reusable ubiquitin molecules and peptides of 5 to 15 amino acids. Conversion of a protein into a substrate for ubiquitination can in certain cases occur after posttranslational modification or association with ancillary factors. Proteins can also be recognized by an E3 ubiquitin ligase without prior modifications or association.

*Reproduced from Gerads et al., CMLS 54: 253–262 (1998)

FIG. 5

Schematic representation of the human 20S proteasome*

*Reproduced from Gerads et al., CMLS 54: 253–262 (1998)

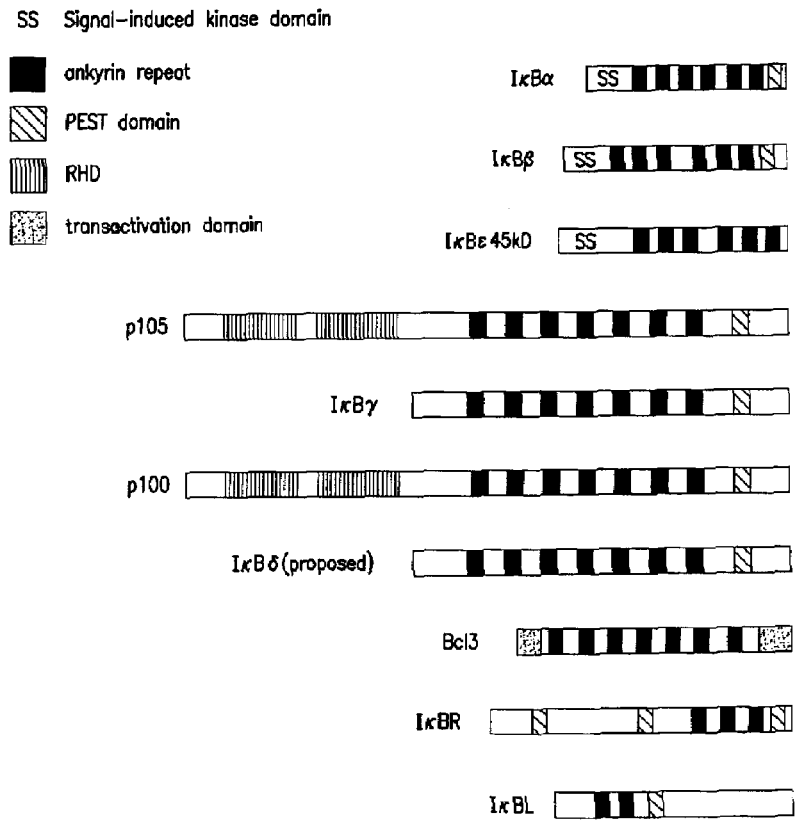

The mammalian IκB family. A schematic representation of the mammalian IKB proteins isolated thus for. The black boxes represent the ankyrin repeat motifs of each protein, and the pair of serine residues which are phosphorylated in response to signalling and are necessary for the inducible degradation of IκB-α, IκB-β and IκB-ε are represented by SS. Also shown are the PEST domains (diagonal shading), the Rel homology domains (RHD) of p105 and p100 (vertical shading) and the transactivation domains of Bcl-3 (striped boxes).

FIG. 7

(1) GENERAL INFORMATION:
    (i) APPLICANT: Children's Medical Center Corporation
    (ii) TITLE OF INVENTION: Synducin Medicated Modulation of Tissue Repair
    (iii) NUMBER OF SEQUENCES: 4
    (iv) CORRESPONDENCE ADDRESS:
        (A) ADDRESSEE: Patrea L. Pabst
        (B) STREET: 2800 One Atlantic Center
                    1201 West Peachtree
        (C) CITY: Atlanta
        (D) STATE: Georgia
        (E) COUNTRY: USA
        (F) ZIP: 30309-3450
    (v) COMPUTER READABLE FORM:
        (A) MEDIUM TYPE: Floppy disk
        (B) COMPUTER: IBM PC compatible
        (C) OPERATING SYSTEM: PC-DOS/MS-DOS
        (D) SOFTWARE: PatentIn Release #1.0, Version #1.25
    (ix) TELECOMMUNICATION INFORMATION:
        (A) TELEPHONE: (404)-873-8794
        (B) TELEFAX: (404)-815-8795
(2) INFORMATION FOR SEQ ID NO:1:
    (i) SEQUENCE CHARACTERISTICS:
        (A) LENGTH: 39 amino acids
        (B) TYPE: amino acid
        (D) TOPOLOGY: linear
    (ii) MOLECULE TYPE: peptide
    (iii) HYPOTHETICAL: NO
    (iv) ANTI-SENSE: NO
    (x) PUBLICATION INFORMATION:
        (A) AUTHORS: Lee, Jong-Youn
                     Boman, Hans G.
                     Mutt, Viktor
                     Jornvall, Hans
        (B) TITLE: Novel Polypeptides And Their Use
        (C) JOURNAL: PCT WO 92/22578
        (G) DATE: 12/23/92
        (K) RELEVANT RESIDUES IN SEQ. ID NO:1: FROM 1 TO 39
    (xi) SEQUENCE DESCRIPTION: SEQ ID NO:1:

Arg Arg Arg Pro Arg Pro Pro Tyr Leu Pro Arg Pro Arg Pro Pro Pro
     1               5                  10                  15

Phe Phe Pro Pro Arg Leu Pro Pro Arg Ile Pro Pro Gly Phe Pro Pro
                    20                  25                  30

Arg Phe Pro Pro Arg Phe Pro
                    35

FIG. 8

METHOD FOR PR-39 PEPTIDE MEDIATED SELECTIVE INHIBITION OF IκBα DEGRADATION

CROSS REFERENCE

The present application is a Continuation-In-Part of prior pending U.S. patent application Ser. No. 09/276,868 filed Mar. 26, 1999 and Ser. No. 09/426,011 filed Oct. 25, 1999.

RESEARCH SUPPORT

The research effort for the invention was supported in part by the National Institutes of Health, grants HL 53793 and HL 56993 (MS), DK 31396 (MS), GM51923 and GM 46147 (ALG), F32HL 10013 (RV), and in part by a grant from Chiron Corporation. The government has certain rights in the invention.

FIELD OF THE INVENTION

The present invention is concerned generally with the Rel/NFκB family of transcription factors within viable cells comprising living tissues and organs; and is particularly directed to proteasome mechanisms regulated by PR-39 peptides which result in a selective inhibition of IκBα degradation on-demand and may be used for controlled suppression of NFκB transcription factor activity and NFκB-dependent gene expression.

BACKGROUND OF THE INVENTION

Degradation of proteins in mammalian cells proceeds via two distinct pathways, the lysosome-dependent and proteasome-dependent systems. The proteasome-dependent system catalyzes the hydrolysis of proteins marked for degradation typically by conjugation to ubiquitin, but also can degrade certain non-ubiquitinated proteins as well.

Proteasome-mediated degradation is also a principal means for controlling the intracellular levels of most cell proteins, including the recognized major regulators of gene expression such as NFκB transcription factor; the inhibitor protein IκBα; hypoxia-inducing factor (HIF)-1a; protooncogenes c-Fos, c-Jun and c-Mos; and the various cyclins. See for example: Whiteside, S. T. and A. Israel, *Semin. Cancer Biol.* 8: 75–82 (1997); Srinivas et al., *J. Biol. Chem.* 273: 18019–18022 (1998); Salceda, S. and J. Caro, *J. Biol. Chem.* 272: 22642–22647 (1997); Huang et al., *Proc. Natl. Acad. Sci. USA* 95: 7987–7992 (1998); He et al., *J. Biol. Chem.* 273: 25015–25019 (1998); and Pahl, H. L. and P. A. Baeverle, *Curr. Opin. Cell Biol.* 8: 340–347 (1996). Furthermore, the smaller-sized peptides generated by the proteasome during the course of protein breakdown are often biologically active; for example, some peptides are presented as antigens on the class I major histocompatibility complex (MHC) [Rock, K. L. and A. L. Goldberg, *Annu. Rev. Immunol.* 17: 739–779 (1999)]. These degradation products thus can cause different effects and major consequences in a variety of cellular processes, many of which have substantive clinical value.

In particular, NFκB-dependent gene expression is recognized as playing an important role in a number of biological processes of major medical importance including immune, inflammatory and anti-apoptotic responses [Baeuerle, P. A. and D. Baltimore, *Cell* 87: 13–20 (1996); Beg, A. A. and D. Baltimore, *Science* 274: 782–784 (1996); and Antwerp et al., *Science* 274: 787–789 (1996)]. NFκB is a dimer molecule composed of the p50 and p65 (RelA) monomer subunits; and binding of this dimer complex to IκB inhibitor protein in a cytosol is believed to be the main cellular mechanism preventing NFκB-dependent transcription of genes under normal conditions. A number of different extracellular stimuli (including TNFα, Il-1 and lipopolysaccharide) can trigger NFκB transcription factor activation, most notably by causing a rapid degradation of IκB inhibitor protein by the ubiquitin (Ub)-proteasome degradation pathway.

Several steps necessary for proteasome-mediated IκBα degradation to occur have been identified. These include: phosphorylation of IκBα at two sites by a specific IκBα kinase of the SCF1 family [Whiteside, S. T. and A. Ismael, *Semin. Cancer Biol.* 8: 75–82 (1997); Chen et al., *Cell* 84: 853–862 (1996)]; the ubiquitination of the phosphorylated IκBα by a specific E3 enzyme complex [Suzuki et al., *Biochem. Biophys. Res. Comm.* 256: 121–126 (1996); Spencer et al., *Genes Dev.* 13: 284–294 (1999); Kroll et al., *J. Biol. Chem.* 274: 7941–7945 (1999); Yaron et al., *Nature* 396: 590–594 (1998); and Gonen et al., *J. Biol. Chem.* 274: 14923–14830 (1999)]; and the subsequent binding to VCP (valosin-containing protein) that results in a physical link between the ubiquitinated IκBα and the proteasome.

Separate and distinct from these events is the PR-39 protein. PR-39 is a highly basic arginine/proline-rich peptide originally isolated from porcine intestine on the basis of its anti-bacterial activity [Agerbeth et al., *Eur. J. Biochem.* 202: 849–854 (1991)]. The PR-39 peptide is secreted in a preproprotein form that includes a canonical leader sequence and rapidly undergoes cleavage of the N-terminal portion to generate the mature form composed of the 39 C-terminal amino acids [Gudmundsson et al., *Proc. Natl. Acad. Sci. USA* 92: 7085–7095 (1995)]. While the sequence of the N-terminal part of the prepro-protein is highly homologous to the cathelin gene family members, the sequence of the 39 C-terminal amino acids that make up the mature peptide, has no homology to any other known protein.

Research investigations have shown that PR-39 protein can rapidly cross cell membranes; and, by virtue of its proline-rich composition, may interact with SH3 domains of $p47^{phox}$ and $p130^{Cas}$ [Ross et al., *Proc. Natl. Acad. Sci. USA* 93: 6014–6018 (1996); and Chan, Y. R. and R. L. Gallo, *J. Biol. Chem.* 273: 28978–28985 (1998)]. The PR-39 peptide (predominantly produced by blood-derived macrophages) is found at the sites of active inflammation including skin wounds and myocardial infarction and is seen as playing an important role by inducing expression of heparan sulfate-carrying core proteins, syndecan 1 and 4 [Li et al., *Circ. Res.* 81: 785–796 (1997); and Gallo et al., *Proc. Natl. Acad. Sci. USA* 91: 11035–11039 (1994)] and inhibiting degradation of the hypoxia-inducible factor (HIF)-1α protein. However, the molecular events and mechanism of action involved in this peptide's actions remain largely unknown.

Accordingly, although there have been many investigations, publications, and developments of these various entities, there remains a general ignorance and failure of understanding by research investigators and clinicians alike regarding useful and effective specific means and methods for suppressing NFκB-dependent gene expression on-demand within living cells, tissues, and organs. Thus, while the value and desirability of selectively controlling NFκB transcription factor activity—especially within cells at localized tissue areas on an as-needed basis for individual subjects—is well recognized, these aims have remained a long-sought goal yet to be achieved to date in a practical manner.

SUMMARY OF THE INVENTION

The present invention has multiple aspects and uses. A first aspect provides a method for selectively inhibiting degradation of IκBα within a targeted collection of viable cells in-situ, said method comprising the steps of:

identifying a collection of cells comprising viable cells in-situ as a target for inhibiting IκBα degradation;

providing means for effecting an introduction of at least one member selected from the group consisting of the PR-39 oligopeptide collective to the cytoplasm of said targeted collection of cells;

introducing at least one member of the PR-39 oligopeptide collective to the cytoplasm of said targeted collection of cells using said effecting means;

allowing said introduced PR-39 oligopeptide collective member to interact with such IκBα and proteasomes as are present within the cytoplasm of said targeted collection of cells whereby (a) at least some of the proteasomes interact with said PR-39 oligopeptide collective member, (b) at least a part of the proteolytic activity mediated by said interacting proteasomes becomes selectively altered, and (c) the selectively altered proteolytic activity of said proteasomes results in a marked inhibition of IκBα degradation in-situ within the cytoplasm of said targeted collection of viable cells.

A second aspect of the invention provides a method for decreasing the activity of NFκB transcription factor in-situ within a collection of viable cells, said method comprising the steps of:

identifying a collection of cells comprising viable cells in-situ as a target for decreased NFκB activity;

providing means for effecting an introduction of at least one member selected from the group consisting of the PR-39 oligopeptide collective to the cytoplasm of said targeted collection of cells;

introducing at least one member of the PR-39 oligopeptide collective to the cytoplasm of said targeted collection of cells using said effecting means;

allowing said introduced PR-39 oligopeptide collective member to interact with such IκBα and proteasomes as are present within the cytoplasm of said targeted collection of cells whereby (a) at least some of the proteasomes interact with the PR-39 oligopeptide collective member, (b) at least a part of the proteolytic activity mediated by said proteasomes becomes selectively altered by said interaction, (c) the selectively altered proteolytic activity of said proteasomes results in a marked reduction of IκBα degradation in-situ within the cytoplasm of said targeted collection of cells; and (d) said reduction of IκBα degradation results in a decrease in activity for such NFκB transcription factor as is present intracellularly.

BRIEF DESCRIPTION OF THE FIGURES

The present invention may be more fully understood and better appreciated when taken in conjunction with the accompanying drawing, in which.

DETAILED DESCRIPTION OF THE INVENTION

Figure 1:
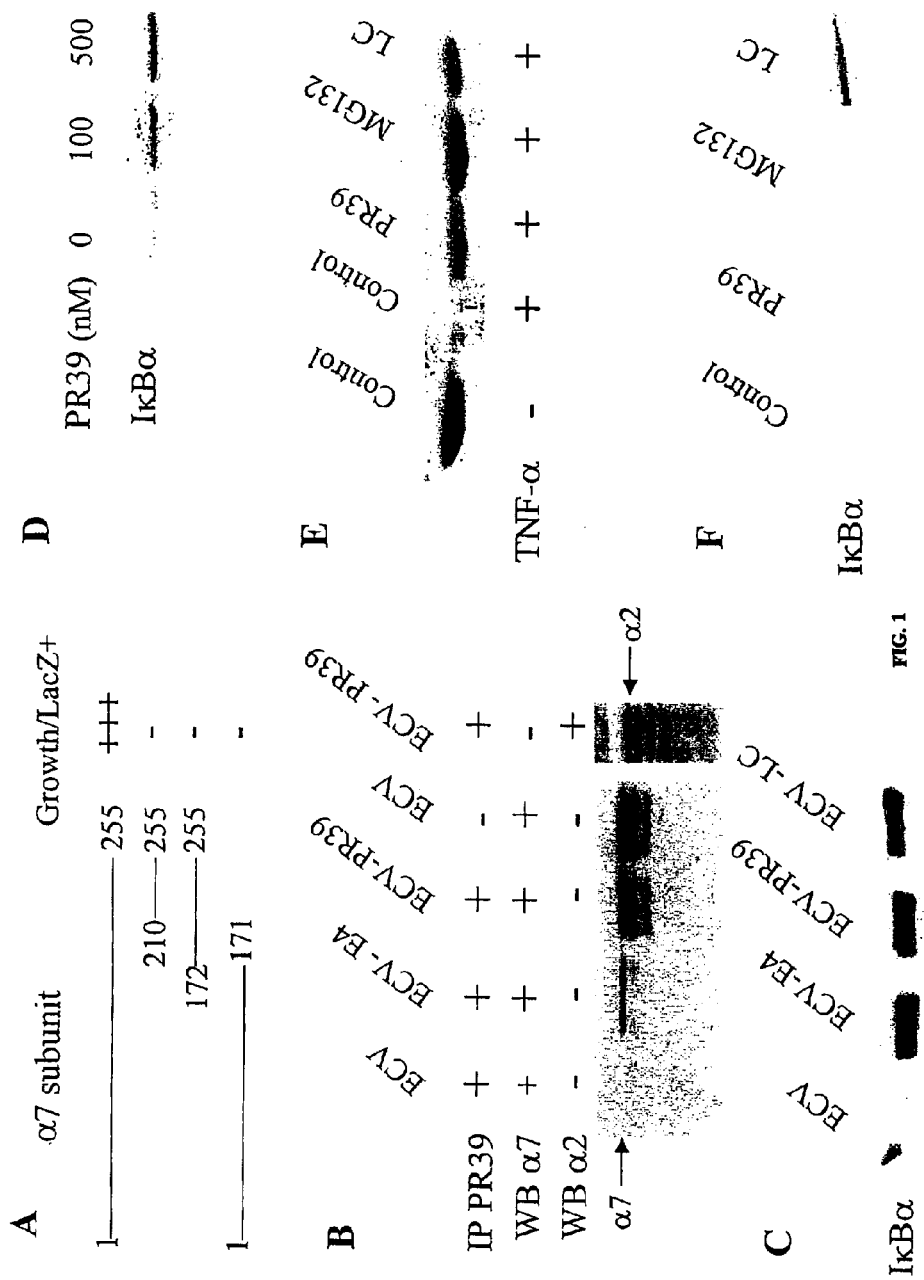
FIGS. 1A–1F are presentations of empirical data showing the interaction between PR-39 peptide and proteasomes and the effect of such interaction on IκBα degradation and NFκB activity.

The present invention is a method for selectively inhibiting the degradation of IκBα protein via the purposeful introduction of native PR-39 peptide or a member of the PR-39 derived oligopeptide family to the cytoplasm of viable cells in-situ. The PR-39 peptide or the derived member of the oligopeptide family will interact with such IκBα protein and proteasomes as are present intracellularly; and the consequence of PR-39 peptide/IκBα/proteasome interactions is the marked inactivation of NFκB transcription factor such that intracellular NFκB-dependent gene expression is diminished and suppressed in-situ.

A number of major benefits and advantages are therefore provided by the means and methods comprising the present invention. These include the following:

1. The present invention provides means for selective inhibition of IκBα protein degradation in-situ. By definition, therefore, both in-vivo and in-vitro circumstances of use and application are envisioned and expected. Moreover, the viable cells which are the location of PR-39 peptide, IκBα and proteasome interactions, alternatively may be isolated cells; be part of living tissues comprising a variety of different cells such as endothelial cells, fibrocytes and muscle cells; and may also comprise part of specific organs in the body of a living human or animal subject. While the user shall choose the specific conditions and circumstances for practicing the present invention, the intended scope of application and the envisioned utility of the means and methods described herein apply broadly to living cells, living tissues, functional organs and systems, as well as the complete living body unit as a viable whole.

2. The present invention has a variety of different applications and uses. Of clinical and medical interest and value, the present invention provides the opportunity to selectively control NFκB-dependent gene expression in tissues and organs in a living subject which has suffered defects or has undergone anoxia or infarction. A typical clinical instance is the myocardial infarction or chronic myocardial ischemia of heart tissue in various zones or areas of a living human subject. The present invention thus provides opportunity and means for specific site control of gene expression in NFκB-dependent cells. The present invention also has major research value for research investigators in furthering the quality and quantity of knowledge regarding the mechanisms controlling NFκB-initiated gene expression under a variety of different conditions and circumstances.

3. The present invention envisions and permits a diverse range of means for introducing native PR-39 peptide or a shorter-length peptide of the oligopeptide family to a diverse range of different cells at a specific location, site, tissue, organ, or system in the living body. A variety of different routes of administration are available to the practitioner which will vary with the type of cells and their location; and a wide and useful choice of delivery systems are conventionally available, and in accordance with good medical practice, are adaptable directly for use. In this manner, not only are the means for PR-39 peptide introduction under the control of the user, but also the manner of application and the location of PR-39 peptide introduction can be prechosen and controlled.

I. Underlying Mechanisms for Initiating a Reduction of IκBα Degradation

The present invention utilizes and relies upon novel and previously unknown direct and indirect mechanisms of interaction between PR-39 peptide (or its shorter-length homologs) and proteasomes in-situ as the basis for reducing IκBα protein degradation in cells, living tissues, and organs. Evidence of such intracellular interactions is provided by the experiments and empirical data described hereinafter. Such interactions between proteasomes, ubiquitinated IκBα and the PR-39 family of peptides collectively (of any size) are previously unknown; in fact, no meaningful relationship or interaction between any peptide whatsoever and control of intracellular proteasome function has ever been proposed or envisioned before the present invention was conceived or demonstrated empirically.

As shown experimentally hereinafter, the PR-39 peptide (and the shorter-length PR-39 derived oligopeptide family members) when introduced into the cytoplasm of viable cells will interact, directly and indirectly, with proteasomes. In some instances, the interaction between the collective of PR-39 oligopeptides and the proteasome is direct. One example is a direct binding of PR-39 peptide with the α7 subunit of the proteasome. In these instances, no intermediaries or cofactors are involved in the binding reaction; and such direct binding interactions result in a selective inactivation and inhibition of proteasome function intracellularly such that expression of certain proteins such as HIF-1α is increased and stimulation of angiogenesis subsequently occurs.

In addition, however, alternative mechanisms of interaction for members of the PR-39 peptide collective (including native PR-39 and its substituted or homologous forms) in addition to and other than direct inactivation of a proteasome subunit concurrently exist and are often in effect in-situ. As an examplary and representative instance illustrating an alternative mechanism of action, the experiments and empirical data presented hereinafter demonstrate that: PR-39 peptide acts as a selective inhibitor of IκBα protein degradation by proteasomes; and that PR-39 peptide selective inhibition of IκBα degradation is rapidly reversible (unlike the action of known inhibitory compounds such as lactacysin); and that, even in the presence of PR-39 peptide, the intracellular expression of other proteasome-regulated proteins (such as p105 and p50) NFκB remain unchanged. These empirically documented findings are meaningful evidence of, harmonious with, and consistent demonstrations of indirect mechanisms of interaction rather than any direct action effect. Accordingly, the selective and reversible nature of PR-39 peptide activity with regard to inhibiting IκBα degradation is deemed to be due to a prevention of recognition for the ubiquitinated IκBα complex by the proteasome and/or a physical blockage of the complex's entry into the interior of the proteasome in-situ. These are indirect mechanisms of action in that the PR-39 protein is believed to interact with the ubiquitinated-IκBα complex rather than affect the proteasome itself; and such indirect mechanisms exist concurrently with and are functional alternatives available on-demand in addition to any direct action/inactivation mechanisms.

To initiate a demonstrable mechanism of action (indirect or direct) and effect in-situ, the introduction of native PR-39 peptide (or one of its substituted forms or its shorter-length analogs or homologs) is the sole necessary prerequisite. Only the presence of sufficient PR-39 peptide (or any of its substituted or homologic equivalents) quantitatively to interact selectively with such proteasomes are as present intracellularly within viable cells is needed to invoke the PR-39 effect under both in-vivo conditions and in-vitro use circumstances.

The methodology and means provided by the present invention for selectively inhibiting IκBα proteolysis, reducing NFκB activity, and decreasing NFκB-dependent gene expression within viable cells is therefore directed at and focused upon the intracellular degradation capability and function of proteasomes. Such selective inhibition and/or disruption of proteasome-mediated protein degradation is achieved via the introduction of native PR-39 peptide or a member of the shorter-length PR-39 derived oligopeptide family in any regimen of treatment.

II. Proteasomes

The proteasome is a component of the ubiquitin-proteasome-dependent proteolysis system. This system plays a major role in the turnover of intracellular proteins, of misfolded proteins, and in the selective degradation of key proteins. Controlled protein degradation is an important and efficient way to remove nonfunctional proteins and/or to regulate the activity of key proteins. Target proteins are selectively recognized by the ubiquitin system and subsequently marked by covalent linkage of multiple molecules of ubiquitin, a small conserved protein. The polyubiquitinated proteins are degraded by 26S proteasome. This complex, however, is composed of two large subcomplexes: the 20S proteasome constituting the proteolytic core and the 19S regulatory complex which confers polyubiquitin binding and energy dependence. A simplified scheme of the ubiquitin pathway is depicted by Flow Scheme A below.

A substantial quantum of research has been conducted to understand the architecture, assembly, and molecular biology of the proteasome. Merely representative of scientific publications in this field are the following, the individual texts of which are expressly incorporated by reference herein: Goldberg et al., *Biol. Chem.* 378: 131–140 (1997); Tanaka, K., *Biochem. Biophys. Res. Commun.* 247: 537–541 (1998); Baumeister et al., *Cell* 92: 367–380 (1998); Gerards et al., *CMLS* 54: 253–262 (1998); Maurizi, M. R., *Curr. Biol.* 8: R453–R456 (1998); Rechsteiner et al., *J. Biol. Chem.* 268: 6065–6068 (1993); Gerards et al., *J. Mol. Biol.* 275: 113–121 (1998); Fenteany, G. and S. Schreiber, *J. Biol. Chem.* 273: 8545–8548 (1998); and Oikawa et al., *Biochem. Biophys. Res. Commun.* 246: 243–248 (1998).

The 20S Proteasome

The degrading component in ubiquitin-dependent proteolysis is the 26S proteasome. The catalytic core of this complex is the 20S proteasome, which is highly conserved and can be found in eukaryotes, archaebacteria, and some eubacteria. In eukaryotes, the amount of proteasomes can constitute up to 1% of the cell content, depending on the average protein breakdown rates of the organ. Proteasomes are localized in the nucleus and the cytosol, sometimes colocalizing or associating with the cytoskeleton. [See for example: Hilt, W. and D. H. Wolf, *Trends Biochem. Sci.* 21: 96–102 (1996); Ciechanover, A., *Cell* 79: 13–21 (1994); Jentseh, S. and S. Schlenker, *Cell* 82: 881–884 (1995); Coux et al., *Annu. Rev. Biochem.* 65: 807–847 (1996); Dahlmann et al., *FEBS Lett.* 251: 125–131 (1989); Tamura et al., *Curr. Biol.* 5: 766–774 (1995); Machiels et al., *Eur. J. Cell Biol.* 66: 282–292 (1995); Scherrer, K. and F. Bey, *Prog. Nucleic Acid Res. Mol. Biol.* 49: 1–64 (1994); and Gerards et al., *CMLS* 54: 253–262 (1998)].

The first description of a "cylinder-shaped" complex with proteasome-like features dates back to the late 1960s. The plethora of names given to it subsequently is a reflection of the problems that were encountered over a period of two decades in trying to define its biochemical properties and cellular functions. Enzymological studies revealed an array of distinct proteolytic activities and led to a consensus name, 'multicatalytic proteinase'. This name, however, was soon replaced by a new one, the 'proteasome' emphasizing its character as a molecular machine.

At about the same time, it was found that the occurrence of proteasomes was not restricted to eukaryotic cells. A compositionally simpler, but structurally strikingly similar proteolytic complex was found in the archaeon *Thermoplasma acidophilum*, which later took a pivotal role in elucidating the structure and enzymatic mechanism of the proteasome.

Nomenclature

The 20S proteasome was independently discovered by groups working in different fields, and hence was given a variety of different names. In 1970, Scherrer and colleagues observed ring-shaped particles in ribosome-free messenger RNA (mRNA) preparations [Sporh et al., *Eur. J. Biochem.* 17: 296–318 (1970)]. Subsequently, in 1979, DeMartino and Goldberg isolated a 700-kDa 'neutral protease' from rat liver [DeMartino, G. N. and A. L. Goldberg, *J. Biol. Chem.* 254: 3712–3715 (1997)]. Then, in 1980 Wilk and Orlowski isolated a large protease complex from the pituitary that possessed three different catalytic activities. They called it multicatalytic protease [Wilk, S. and M. Orlowski, *J. Neurochem.* 35: 1172–1182 (1980); Wilk, S. and M. Orlowski, *J. Neurochem.* 40: 842–849 (1983)]. Later, Monaco and McDevitt immunoprecipitated complexes consisting of low molecular weight proteins (LMPs) with a possible role in antigen presentation [Monaco, J. J. and H. O. McDevitt, *Nature* 309: 797–799 (1984)]. Also, in 1984 this particle was called prosome, referring to its presumed role in programming mRNA translation [Schmid et al., *EMBO* 3: 29–34 (1984)]. Altogether, this complex has been given 21 different names in the literature. Since all particles were shown to be identical the name 'proteasome' (which is now generally accepted) was proposed first, referring to its proteolytic and particulate nature [Arrigo et al., *Nature* 331: 192–194 (1988); Faulkenburg et al., *Nature* 331: 190–192 (1988); Brown et al., *Nature* 353: 355–357 (1991)].

Overall Characteristics and Properties

The 20S proteasome is the major cytosolic protease in eukaryotic cells and is the proteolytic component of the ubiquitin-dependent degradative pathway. Proteasomes are also found in some, but not all, archaebacteria and eubacteria, and in eukaryotes. True proteasomes are composed of 28 subunits, 14 each of two different classes—non-catalytic alpha ($\alpha$) and catalytically-active beta ($\beta$) subunits. The subunits are arranged in rings of seven subunits, all of a single type. The 20S proteasome is a stack of four rings, two inner beta rings flanked by the alpha rings. The junction between the beta rings produces a remarkable structural feature of proteasomes—an interior aqueous cavity large enough to accommodate about 70 kDa of protein and accessible only through narrow axial channels in the rings. The catalytic sites are located on the beta subunits within the aqueous cavity. Isolation of the catalytic sites in this way, and the limited access via narrow channels, serves to compartmentalize proteolysis, allowing degradation of only those proteins that can be actively translocated into the interior of the proteasome.

Structure and Subunit Components

The 20S proteasome has a cylindrical or barrel-like structure, typically 14.8 nm in length and 11.3 nm in diameter. It is composed of 28 subunits and arranged in four stacked rings, resulting in a molecular mass of about 700 kDa. This overall structural architecture is conserved from bacteria to man.

In eukaryotes, including humans, 14 different subunits, ranging from 21 kDa to 32 kDa, are present in the complex. Based on the sequence homology with the *T. acidophilum* $\alpha$- or $\beta$-subunit, the eukaryotic subunits are divided into $\alpha$-type and $\beta$-type, respectively [Zwicki et al., *Biochemistry* 31: 964–972 (1992); Heinemeyer et al., *Biochemistry* 33: 12229–12237 (1994); Coux et al., *Mol. Gen. Genet.* 245: 769–780 (1994)]. Table 1 shows some characteristics and alternative names of the subunits of the human and yeast 20S proteasome using the older and the new nomenclature proposed by Groll and coworkers [Groll et al., *Nature* 386: 463–471 (1997)]. Immuno-electron microscopy (EM) studies also revealed that the eukaryotic $\alpha$-type subunits reside in the outer rings and the $\beta$-type subunits in the inner rings. Furthermore, these studies indicated that in the eukaryotic 20S proteasome seven different subunit constitute a ring, each subunit located at a defined position [Kopp et al., *J. Mol. Biol.* 229: 14–19 (1993); Kopp et al., *J. Mol. Biol.* 248: 264–272 (1995); Schauer et al., *J. Struct. Biol.* 111: 135–147 (1993); Kopp et al., *Proc Natl Acad Sci USA* 94: 2939–2944 (1997)]. Therefore, the eukaryotic proteasome assembles as an $\alpha_{1-7}\beta_{1-7}\beta_{1-7}\alpha_{1-7}$ particle. The typical human structure and assembly is illustrated by Table 2.

TABLE 1

Nomenclature and molecular masses of proteasomal subunits

| Systematic name | Human gene | Yeast gene | Molecular mass of human subunit (kDa) |
|---|---|---|---|
| $\alpha1$ | HsPROS27 HsIota | C7 PRS2 | 27.4 |
| $\alpha2$ | HsC3 | Y7 | 25.9 |
| $\alpha3$ | HsC9 | Y13 | 29.5 |
| $\alpha4$ | XAPC7 HsC6 | PRE6 | 27.9 |
| $\alpha5$ | HsZeta | PUP2 | 26.4 |
| $\alpha6$ | HsPROS30 HsC2 | PRE5 | 30.2 |
| $\alpha7$ | HsC8 | C1 PRS1 | 28.4 |
| $\beta1$ | HsDelta Y | PRE3 | 25.3 (21.9) |
| $\beta1i$ | LMP2 | | 23.2 (20.9) |
| $\beta2$ | Z | PUP1 | 30.0 (24.5) |
| $\beta2i$ | MECL1 | | 28.9 (23.8) |
| $\beta3$ | HsC10-11 | PUP3 | 22.9 |
| $\beta4$ | HsC7-1 | PRE1 C11 | 22.8 |
| $\beta5$ | MB1 X | PRE2 | nd (22.4) |
| $\beta5i$ | LMP7 | | 30.4 (21.2) |
| $\beta6$ | HsC5 | C5 PRS3 | 26.5 (23.3) |
| $\beta7$ | HsBPROS26 HsN3 | Pre4 | 29.2 (24.4) |

*Reproduced from Gerards et al., CMLS 54: 253–262 (1998)

Proteolytic Activity

The first report on the multicatalytic properties of the proteasome stems from 1983, when three different proteolytic activities were distinguished: 'trypsin-like', 'chymotrypsin-like' and 'peptidylglutamyl-peptide hydrolase' activity [Wilk, S. and M. Orlowski, *J. Neurochem.* 40: 842–849 (1983)]. These three proteasomal activities refer to peptide bond cleavage at the carboxyl side of basic, hydrophobic and acidic amino acid residues, respectively. They were identified using short synthetic peptide substrates and are believed to be catalyzed at independent sites—in part because the different proteolytic activities respond differentially to various activators and inhibitors. With similar approaches, at least two additional proteolytic activities have been recently described [Orlowski et al., *Biochemistry* 32: 1563–1572 (1993); Orlowski, M., *Biochemistry* 29: 10289–10297 (1990); Rivett, A. J., *Biochem. J.* 291: 1–10 (1993)].

The Progressive Degradation of Protein Substrates

Recent studies have also revealed a fundamental new property of the proteasome that clearly distinguishes it from conventional proteases: i.e., this particle degrades a protein substrate all the way to small peptides, before attacking another protein substrate [Akopian et al., *J. Biol. Chem.* 272: 1791–1798 (1997)]. Because the proteasome's multiple active sites are located in its central chamber and because diffusion of a peptide substrate into this compartment must be a slow process, these particles function in a highly processive fashion; i.e., they have mechanisms of action to bind tightly protein substrates and to make multiple cleavages in the polypeptide before releasing the peptide products. Moreover, the ratio of new peptides generated to the number of substrate molecules consumed is constant during the reaction. In other words, as peptides accumulated, they were not hydrolyzed further, even during prolonged incubations, where up to half of the substrate molecules were consumed. Equally important, the disappearance of these substrate molecules coincided exactly with the appearance of small peptide products [Goldberg et al., *Biol. Chem.* 378: 131–140 (1997)]. These observations, together with the finding that the pattern of the products is independent of time, established that processive degradation is a general feature of the 20S proteasome [Gerard et al., *CMLS* 54: 253–262 (1998)].

The contribution of each individual active center and proteolytic activity to the degradation of longer peptides and complete proteins is presently unknown. Nevertheless, proteasomes are able to cleave behind most amino acids in a protein. Thus, the 20S proteasome is in fact a nonspecific endopeptidase. In addition, however, the generated (degraded) peptides fall into a rather narrow size range of 6 to 10 amino acids in length, demonstrating the existence of a kind of 'molecular ruler'. The average length of the degradation products is typically 7 to 8 amino acids; this finding is in agreement with the distance between the active sites in the proteasome. Similar nonspecific endopeptidase activity and size distribution of degration products from whole proteins was observed for proteasomes generally and by proteasomes of human origin in particular.

Other features of the 20S proteasome degradation are also unique. While unfolded peptides are usually digested, most native proteins are resistant to proteolytic degradation by the 20S proteasome in vitro. However, denaturation of the substrate protein by oxidation or reduction of disulphide bridges can render it accessible to degradation by proteasomes. Also, small gold particles with a diameter of 2 nm containing unfolded substrate cannot enter the proteasome. These characteristics show that a relatively narrow opening controls access to the inner proteolytic compartment of the proteasome.

III. IκBα Protein and NFκB Transcription Factor

Regulation of the immune and inflammatory responses requires the activation of specific sets of genes by a variety of extracellular signals. These signals include mitogens (e.g., lipopolysaccharide and phorbol myristate acetate), cytokines (e.g., tumor necrosis factor α and interleukin-1β), viral proteins (e.g., the Tax protein of type 1 human T cell leukemia virus), antigens, phosphatase inhibitors (e.g., okadaic acid and calyculin A), and ultraviolet light.

The Rel/NFκB family of transcriptional activator proteins plays an essential role in the signal transduction pathways that link these signals to gene activation [Siebenlist et al., *Annu. Rev. Cell Biol.* 10: 405–455 (1994); Thanos and Maniatis, *Cell* 80: 529–532 (1995); Verma et al., *Gene Dev.* 9: 2723–2735 (1995)]. NFκB (p50/RelA[p65]) and other heterodimeric Rel family proteins are sequestered in the cytoplasm through their association with members of the IκB family of inhibitor proteins. In the case of IκBα, stimulation of cells leads to rapid phosphorylation and degradation of the inhibitor protein. Consequently, NFκB is released and translocates into the nucleus, where it activates the expression of target genes.

NFκB itself is an inducible transcriptional factor which regulates many biologically important processes, such as stress, inflammation, development and immune response [May, M. J. and S. Ghosh, *Immunol. Today* 19: 80–88 (1998)]. The prototypical inducible NFκB complex is a heterodimer of the Rel protein family, consisting of p50 and p65 (also called Rel A) [Baeverle, P. A. and D. Baltimore, *Cell* 87: 13–20 (1996); Baldwin, A. S., *Anno. Rev. Immunol.* 14: 649–681 (1996)]. In the cytoplasmic compartment of many types of cells, NFκB normally exists in an inactive form due to association of its protein inhibitor, termed IκB. IκB prevents the transport of NFκB into the nucleus by masking the nuclear localization signal (NLS) of NFκB [Finco, T. S. and A. S. Baldwin, *Immunity* 3: 253–272 (1995)]. This action is mediated by the multiple, tandemly-repeated ankyrin repeats present on IκB, which are thought to interact with NFκB. To date, there are 9 members in the structurally and functionally related IκB protein family: IκBα, IκBβ, IκBε, IκBγ (-1, -2), Bcl-3, p100, and p105, have been identified [Whiteside, S. T. and A. Israel, *Cancer Biol.* 8: 75–82 (1997)].

It is recognized that IκBα binding with NFκB will cause inactivation of NFκB function. However, phosphorylation of IκBα per se is not sufficient to dissociate NFκB from the latent complex [Palombella et al., *Mol. Cell. Biol.* 15: 1294–1301 (1995)]. Rather, phosphorylation triggers the degradation of IκBα [Brockman et al., *Mol. Cell. Biol.* 15: 2809–2818 (1995); Brown et al., *Science* 267: 1485–1490 (1995)].

Various external stimuli, such as cyotkines including alpha-type tumor necrosis factor (TNFα), viral infection, T-cell and B-cell mitogens, and UV-stress, initiate the immediate removal of IκB from the IκB-(NFκB) complex [May, M. J. and S. Ghosh, *Immunol. Today* 19: 80–85 (1998); Finco, T. S. and A. S. Baldwin, *Immunity* 3: 253–272 (1995)]. The tremendous progress in delineating the molecular mechanisms of the NFκB signaling pathway has revealed that phosphorylation of 2 serine residues (Ser-32 and Ser-36) near the N-terminus of IκBα is essential for targeting IκBα for signal-promoted destruction [Traenckner et al., *EMBO J.* 14: 2876–2883 (1995); Chen et al., *Genes Dev.* 9: 1586–1597 (1995); DiDonato et al., *Mol. Cell. Biol.* 16: 1295–1304 (1996)]. This specific phosphorylation of IκBα is catalyzed by an unusually large, multi-protein kinase complex, termed IκB kinase (abbreviated IKK), with an apparent molecular mass of 700–900 kDa. The phosphorylation of IκBα by an IKK complex is necessary for its poly-ubiquitination at residues Lys-21 and Lys-22 [Scherer et al., *Proc. Natl. Acad. Sci. USA* 92: 11259–11263 (1995); Baldi et al., *J. Biol. Chem.* 271: 376–379 (1996); Rodriguez et al., *Oncogene* 12: 2425–2435 (1996); Spencer et al., *Genes Dev.* 13: 284–294 (1999)]. The ubiquitin (Ub)-proteasome system then plays the next indispensable role for down-regulating IκBα at the physiologic level [Traenckner et al., *EMBO J.* 13: 5433–5441 (1994); Chen et al., *Cell* 84: 853–862 (1996)].

Identification of IKB Activity

When first discovered, NFκB was thought to be a transcription factor specific to β cells. However, by treating cytosolic extracts from other cell types with a mixture of detergents the presence of latent NFκB DNA-binding activity in the cytoplasm was detected. Furthermore, cytoplasmic extracts were found to contain activities that could inhibit NFκB DNA-binding activity. Therefore, the existence of a cytoplasmic inhibitor of NFκB activity, I kappa B (IκB), which would become inactivated upon induction of NFκB activity was proposed [Baeuerle, P. A. and D. Baltimore, *Cell* 53: 211–217 (1988)]. (IκB is also able to dissociate preformed NFκB/DNA complexes, leading to the hypothesis of a role for IκB in the nucleus).

IκB activity was found to be biochemically purifiable as two immunologically distinct activities, α and β, which differ slightly in their molecular weights (37 kDa and 43 kDa, respectively) as well as their mechanism of inactivation: whereas purified IκBα could be inactivated by treatment with various purified kinases, IκBβ could be inactivated by phosphatase treatment [Link et al., *J. Biol. Chem.* 267: 239–246 (1992)]. Recently, a third cytoplasmic IκB protein, IκBε, which controls the activity of a subset of Rel/NFκB transcription complexes, has also been identified [Whiteside et al., *EMBO J.* 16: 1413–1426 (1997)]. cDNAs encoding two other IκB-like proteins, IκBDL and IκBR, have also been isolated, although their relevance to the regulation of NFκB activity remains uncertain [Albertella et al., *Hum. Mol. Genet.* 3: 793–799 (1994); Ray et al., *J. Biol. Chem.* 270: 10680–10685 (1995)]. IκBR is a 52 kDa molecule that is preferentially expressed in epithelial cells.

In addition, the p105 and p100 precursor proteins of the p50 and p52 DNA-binding subunits of NFκB exhibit the properties of IκB molecules, in that they are able to sequester NFκB proteins (in the form of monomers) in the cytoplasm [Rice et al., *Cell* 7: 243–253 (1992)]. The NFκB proteins sequestered by p105 or p100 are not activatable by detergents in vitro.

The C-terminal portion of the p105 protein, IκB-γ, has also been found to exist as a 70 kDa protein in its own right in certain cell types, synthesized from an internal promoter of the same gene [Inoue et al., *Cell* 68: 1109–1120 (1992)], although the function of IκB-γ has only been found in mouse cells to date. In addition, alternative splicing of IκB-γ has been shown to generate two smaller molecules, IκB-γ-1 (63 kDa) and Iκb-γ-2 (55 kDa) which can both inhibit NFκB [Grumont, R. J. and S. Gerondakis, *Proc. Natl. Acad. Sci. USA* 91: 4367–4371 (1994)]. By analogy to IκB-γ, a C-terminal form of p100 has been hypothesized to exist (IκB-δ) [Dobrzanski et al., *Oncogene* 10: 1003–1007 (1995)], but IκB-δ has not been rigorously identified in vivo.

Finally, there exists a nuclear IκB protein, Bcl-3, which can complex with specific dimers (such as p522 and p502) and transactivate κB-dependent transcription in a manner that depends on the type of NFκB complex present [Bours et al., *Cell* 72: 729–739 (1993)].

Thus, there are today nine different vertebrate IκB proteins that have been identified.

Structure of the IκB Molecules

All proteins in the IκB family contain multiple copies of a structural motif known as the ankyrin repeat, which is important for protein-protein interactions (see Table 3). IκB-α, -β and -ε contain six ankyrin repeats that are necessary for interaction with NFκB. Mutagenesis studies have shown that the ankyrin repeats of IκBα interact with NFκB causing NFκB to remain in the cytoplasm by masking the nuclear localization sequence (NLS) situated in the C-terminal region of the Rel homology domain (RHD) [Beg et al., *Genes Dev.* 6: 1899–1913 (1992); Ganchi et al., *Mol. Biol. Cell.* 3: 1339–1352 (1992)].

The different IκB molecules show specificity for binding and inhibiting various Rel/NFκB complexes. For example, IκB-α and IκB-β interact with heterodimers of p50 or p52 complexed with RelA or c-Rel, as well as homodimers and heterodimers of RelA and c-Rel. In contrast, IκB-ε appears to be complexed almost exclusively with dimers that contain only RelA and/or c-Rel proteins. These dimers differ from classical NFκB complexes in their DNA-binding specificity, and thus regulate the activity of different subsets of NFκB-dependent genes.

In addition, IκB-β, IκB-β and IκB-ε contain near their N-terminal a pair of serine residues separated by three amino acids that are essential for the regulation of their ability to inhibit NFκB induction. Finally, IκB-αand IκB-β contain a C-terminal region rich in proline, glutamine, asparate, serine and threonine residues (a so-called PEST domain). The PEST domain is a site for phosphorylation and has been implicated in regulating the stability of IκB as well as playing a role in the ability of IκB to inhibit DNA-binding by Rel/NFκB complexes, perhaps via direct interaction with the DNA-binding domain.

Nuclear Functions of IKB

IκBα, IκBβ and IκBε molecules differ in their response to inducers of NFκB. IκBα is rapidly degraded in response to all inducers of NFκB thus far tested; and is subsequently resynthesized in an NFκB-dependent manner. This latter property (coupled with the observation that IκBα is able to remove preformed NFκB complexes from their cognate binding sites) led to the hypothesis that IκBα plays a role in ensuring the transient nature of the NFκB response. Furthermore, in the case of negative regulation of cytokine expression by glucocorticoids, the induced synthesis of IκBα leads to nuclear translocation of IκBα whereupon it can inhibit the binding of NFκB to its target sites [Arenzana-Seisdedos et al., *Mol. Cell. Biol.* 15: 2689–2696 (1995)]. Nuclear IκB would bind to and remove NFκB complexes from DNA, whereupon a nuclear export sequence (NES) in IκBα (exposed upon binding to NFκB) results in a net explusion of NFκB/IκB complexes from the nucleus [Fritz, C. C. and M. R. Green, *Curr. Biol.* 6: 848–854 (1996)].

Whereas IκBα is rapidly degraded in response to inducers of NFκB activity, IκBβ and IκBε are degraded more slowly. In the case of IκBβ, it has been proposed that this protein regulates the persistent response of a subset of NFκB inducers. The NFκB molecules regulated by IκBβ escape control by IκBα by a novel mechanism: in unstimulated cells, NFκB is associated with a hyperphosphorylated form of IκBβ while in stimulated cells NFκB is found in complexes that contain a hypophosphorylated form of IκBβ. These complexes have an exposed NLS and are insensitive to IκBα inhibition. Furthermore, the ternary NFκB/IκBβ complexes can be found in the nucleus of stimulated cells and are able to bind to DNA. It has therefore been proposed that the hypophosphorylated form of IκBβ acts as a chaperone to protect NFκB from IκBα, allowing NFκB to translocate to the nucleus, whereupon IκBβ is either degraded, or is dissociated from NFκB following binding of NFκB to DNA.

IκBε, which is also degraded slowly but resynthesized shortly afterwards, is thought to control a third type of NFκB response, one that is slow, but transient in nature. Although the expression of IκBε is upregulated following induction of NFκB, and while it exists as multiple phospho-isoforms in unstimulated cells, IκBε has yet to be detected in the nucleus and does not appear to contain an NES.

Inducible Degradation of IκB

While IκBα, IκBβ and IκBε each have distinct functions, their degradation appears to involve a similar mechanism. Each IκB contains in its N-terminal region a pair of serine residues that lie in similar sequence contexts. In the case of IκBα, these serine residues (amino acids 32 and 36 in human IκBα) become phosphorylated by a serine-specific kinase following stimulation. This phosphorylation, which does not dissociate IκBα from NFκB, renders IκBα a substrate for ubiquintination (primarily at lysine residues 21 and 22) which in turn targets the protein for degradation by the 26S proteasome. Although IκBβ and IκBε contain lysine residues in similar positions, these lysines are not absolutely required for ubiquitination to occur. The C-terminal PEST domain also appears important for signal-induced ubiquitination and proteolysis.

Ubiquitin and proteasomes are the principal components of an energy-dependent proteolytic system in eukaryotic cells for such as IκBα destruction. Selective destruction of cellular proteins by this system occurs by two sequential processes. The first is selective marking of candidate IκB proteins for degradation by the covalent attachment of a poly-Ub chain [Aershko, A. and A. Ciechanover, *Annu. Rev. Biochem.* 67: 425–479 (1998)]. The second process is proteolytic attack of poly-ubiquitinated IκB proteins by the 26S proteasome, a eukaryotic ATP-dependent 2-MDa protease complex [Coux et al., *Annu. Rev. Biochem.* 65: 801–847 (1996); Baumeister et al., *Cell* 92: 367–380 (1998); and Tanaka, K. and T. Chiba, *Genes Cells* 3: 485–498 (1998)].

The covalent attachment of Ub through its C-terminal Gly residue to the ε-NH$_2$ group of the Lys residue on substrate proteins is known to be mediated by a cascade of three enzymes, designated E1 (Ub-activating), E2 (Ub-conjugating), and E3 (Ub-ligating) [Kroll et al., *J. Biol. Chem.* 274: 7941–7945 (1999); Suzuki et al., *Biochem. Biophys. Res. Comm.* 256: 121–126 (1999); Chen et al., *Cell* 84: 853–862 (1996); Yaron et al., *Nature* 396: 590–594 (1998)]. A poly-Ub chain is formed by linking the C-terminus of one Ub to a Lys residue within another Ub. The resultant poly-Ub chain acts as a degradation signal for proteolytic attack by the 26S proteasome.

In this pathway, the IκBα protein targeted for degradation is first modified by covalent attachment of Ub, a highly conserved polypeptide of 76 amino acids. Ubiquination is a three-step process. First, Ub is activated by a Ub-activating enzyme (E1); the activated Ub is then transferred to a Ub carrier protein (E2, also referred to as Ub-conjugating enzyme [Ubcl]); finally, Ub is conjugated to a protein substrate by forming an isopeptide bond between the C-terminal glycine residue of Ub and the ε-amino group of one or more lysine residues of the protein substrate. This conjugate step often requires a Ub protein ligase (E3). Multiple molecules of Ub can be ligated to a protein substrate to form multi-Ub chains. These are then recognized by a large ATP-dependent protease, the 26S proteasome, composed of a 20S catalytic core and a 19S regulatory complex.

Ubiquitination of IκBα is regulated by signal-induced phosphorylation at two specific residues, serine residues 32 and 36. Single amino acid substitutions of one or both of these residues abolish the signal-induced phosphorylation and degradation of IκBα in vivo. The same mutations also abolish the okadaic acid-induced phosphorylation and ubiquitination of IκBα in vitro. Relatively little is known about the signal transduction pathways and the kinase(s) responsible for the site-specific phosphorylation of IκBα. Mutants of IκBα lacking S32 and S36 are resistant to induced phosphorylation by a variety of stimuli, suggesting that different signal transduction pathways converge on a specific kinase or kinases.

IV. The PR-39 Oligopeptide Collective

Native PR-39 peptide is a substance belonging to the cathelin family of proteins; the mature peptide is 39 amino acids in length in the naturally occurring state; and the peptide is able to exert a variety of activities and cause different cellular outcomes. Although first identified as a membrane permeating antibacterial peptide found in the intestine of pigs [Agerberth et al., *Eur. J. Biochem.* 202: 849–854 (1991)], this peptide was subsequently isolated from wounds where it could simultaneously reduce infection and influence the action of growth factors, matrix components, and other cellular effectors involved in wound repair [Gallo et al., *Proc. Natl. Acad. Sci. USA* 91: 11035–11039 (1994); Gallo et al., *J. Invest. Dermatel.* 104: 555 (1995)]. The structure and membrane interactions of native PR-39 peptide have also been elucidated [Cariaux et al., *Eur. J. Biochem.* 224: 1019–1027 (1994)] and the complete amino acid sequences of native PR-39 peptide and its various substituted forms have been reported [PCT Publication No. WO 92/22578 published 23 Dec. 1992].

More recently, the native PR-39 peptide was shown to possess a syndecan-inducing activity in furtherance of its wound healing capabilities; and while renamed a "syndicin", was shown to induce cellular production of two specific proteoglycans, syndecan-1 and syndecan-4, within living mesenchymal cells [U.S. Pat. No. 5,654,273]. Overall, native PR-39 peptide has been shown to play a role in several inflammatory events including wound healing and myocardial infarction [Gallo et al., *Proc. Natl. Acad. Sci. USA* 91: 11035–11039 (1994); Li et al., *Circ. Res.* 81: 785–796 (1997)]; and the native peptide has been shown to be taken up rapidly by a number of different cell types including meschymal cells and endothelial cells [Chan, Y. R. and R. L. Gallo, *J. Biol. Chem.* 273: 28978–28985 (1998)].

The PR-39 Peptide Grouping

Native PR-39 peptide is composed of the 39 amino acid sequence shown below (and also by Table 4).

```
PR-39: Arg-Arg-Arg-Pro-Arg-Pro-Pro-Tyr-Leu-Pro-Arg-Pro-Arg-Pro-Pro-Pro-Phe-   [SEQ ID NO: 1]

Phe-Pro-Pro-Arg-Leu-Pro-Pro-Arg-Ile-Pro-Pro-Gly-Phe-Pro-Pro-Arg-Phe-

Pro-Pro-Arg-Phe-Pro
```

As conventionally known and reported [see for example, U.S. Pat. No. 5,654,273], the specific peptide can be substituted using conservative substitutions of amino acids having the same or functionally equivalent charge and structure, except for the required amino acid sequence "Arg-Arg-Arg" at the N-terminus and the intermediate amino acid sequences "Pro-Pro-X-X-Pro-Pro-X-X-Pro" and "Pro-Pro-X-X-X-Pro-Pro-X-X-Pro" where X can be substituted freely using any amino acid. Thus, all of the preferred substituted amino acid sequences are of about the same size and each differ from the native PR-39 peptide sequence only by substitutions in the intermediate portions of the structure.

The PR-39 Derived Oligopeptide Family

In addition to the conventionally known native PR-39 peptide amino acid residue sequence and its readily recognizable substituted forms as described above, an entirely novel and unforeseen family of PR-39 derived oligopeptide structures is provided by the present invention for use. This previously unknown family of PR-39 derived oligopeptides is constituted of members which individually will cause a selective inhibition of proteasome-mediated degradation of peptides in-situ after introduction intracellularly to a viable cell.

Each member of this PR-39 derived oligopeptide family presents characteristics and properties which are commonly shared among the entire membership. These include the following:

(i) each peptide sequence is less than 39 amino acid residues in length in every embodiment, and preferably is less than 20 residues in size in the best mode;

(ii) each short-length peptide sequence is at least partially homologous (or analogous) with the N-terminal amino acid residues of the native PR-39 peptide, and preferably is completely identical or markedly similar to the N-terminal end residues of the native PR-39 peptide;

(iii) each short-length peptide is able to interact in-situ with at least a part of such proteasomes as are present within the cytoplasm of the cell; and (iv) each short-length peptide sequence is able to alter markedly the proteolytic activity of proteasomes such that a selective increased expression of specific proteins (such as IκBα and HIF-1α) occurs in-situ.

Merely as illustrative examples and preferred embodiments of the broad membership constituting this PR-39 derived oligopeptide family, the members comprising 15, 11 and 8 amino acid residues respectively in length are presented below as the PR15, PR11, and PR8 entities respectively. Note also that some substituted analogs of these shorter length entities provide biologically active formats. For example, the addition of an amino group in N-terminal opposition or the addition of an acetyl group in the C-terminal position stabilizes and enhances activity of PR11. For comparison purposes only, the complete amino acid sequence of the native PR-39 peptide is presented as well.

```
          1   2   3   4   5   6   7   8   9   10  11  12  13                  [SEQ ID NO: 2]
PR-39:Arg-Arg-Arg-Pro-Arg-Pro-Pro-Tyr-Leu-Pro-Arg-Pro-Arg- 14  15  16  17  18  19  20  21  22  23  24  25  26
      Pro-Pro-Pro-Phe-Phe-Pro-Pro-Arg-Leu-Pro-Pro-Arg-Ile- 27  28  29  30  31  32  33  34  35  36  37  38  39
      Pro-Pro-Gly-Phe-Pro-Pro-Arg-Phe-Pro-Pro-Arg-Phe-Pro

PR-15:1   2   3   4   5   6   7   8   9   10  11  12  13  14  15            [SEQ ID NO: 3]
      Arg-Arg-Arg-Pro-Arg-Pro-Pro-Tyr-Leu-Pro-Arg-Pro-Arg-Pro-Pro

PR-11:1   2   3   4   5   6   7   8   9   10  11                            [SEQ ID NO: 4]
      Arg-Arg-Arg-Pro-Arg-Pro-Pro-Tyr-Leu-Pro-Arg

PR-8:1   2   3   4   5   6   7   8                                         [SEQ ID NO: 5]
      Arg-Arg-Arg-Pro-Arg-Pro-Pro-Tyr
```

The PR-39 Oligopeptide Collective

Terminology and nomenclature often pose problems for the reader as to what precisely is meant. Accordingly, for definitional purposes, avoidance of ambiguities, and clarity of understanding, the following terms and titles will be employed herein. The term "PR-39 peptides grouping" includes by definition the native PR-39 structure and all substituted forms conventionally known of the naturally occurring 39 length amino acid sequence. In distinction, the term "PR-39 derived oligopeptide family" and its members includes by definition all the previously unknown shorter-length homologs and analogs as well as substituted forms of the native PR-39 structure as described above. Finally, the umbrella term and category title "PR-39 oligopeptide collective" includes by definition both the 'PR-39 peptide grouping' as well as the 'PR-39 derived oligopeptide family' members, and identifies any and all individual structures falling into either of the two subset categories.

TABLE 4

(1) GENERAL INFORMATION:
    (i) APPLICANT: Children's Medical Center Corporaton
    (ii) TITLE OF INVENTION: Synducin Mediated Modulation of
Tissue Repair
    (iii) NI.ThiBBR OF SEQUENCES: 4
    (iv) CORRESPONDENCE ADDRESS:
        (A) ADDRESSEE: Patrea L. Pabst
        (B) STREET: 2800 One Atlantic Center
                    1201 West Peachtree
        (C) CITY: Atlanta
        (D) STATE: Georgia
        (E) COUNTRY: USA
        (F) ZIP: 30309-3450
    (v) COMPUTER READABLE FORM:
        (A) MEDIUM TYPE: Floppy disk
        (B) COMPUTER: IBM PC compatible
        (C) OPERATING SYSTEN: PC-DOS/MS-DOS
        (D) SOFTWARE: PatentIn Release #1.0, Version #1.25
    (ix) TELECOMMUNICATION INFORMATION:
        (A) TELEPHONE: (404)-873-8794
        (B) TELEFAX: (404)-815-8795
(2) INFORMATION FOR SEQ ID NO:1:
    (i) SEQUENCE CHARACTERISTICS:
        (A) LENGTH: 39 amino acids
        (B) TYPE: amino acid
        (D) TOPOLOGY: linear
    (ii) MOLECULE TYPE: peptide
    (iii) HYPOTHETICAL: NO
    (iv) ANTI-SENSE: NO
    (x) PUBLICATION INFORMATION:
        (A) AUTHORS: Lee, Joug-Youn
                     Boman, Hans G.
                     Mutt, Viktor
                     Jornvall, Hans
        (B) TITLE: Novel Polypeptides And Their Use
        (C) JOURNAL: PCT WO 92/22578
        (D) DATE: 12/23/92
        (K) RELEVANT RESIDUES IN SEQ ID NO:1: FROM 1 TO 39
    (xi) SEQUENCE DESCRIPTION: SEQ ID NO:1:
    Arg Arg Arg Pro Arg Pro Pro Tyr Leu Pro Arg Pro Arg Pro
Pro Pro
     1               5                  10
15

Phe Phe Pro Pro Arg Leu Pro Pro Arg Ile Pro Pro Gly Phe
Pro Pro
                20                  25                  30

Arg Phe Pro Pro Arg Phe Pro
            35      [SEQ ID NO: 6]

Synthesis

The PR-39 peptide can be synthesized using standard amino acid synthetic techniques. An example is the conventionally used solid phase synthesis [Merrifield, J., *J. Am. Chem. Soc.* 85: 2149 (1964)] described in U.S. Pat. No. 4,244,946, wherein a protected alpha-amino acid is coupled to a suitable resin, to initiate synthesis of a peptide starting from the C-terminus of the peptide. Other methods of peptide synthesis are described in U.S. Pat. Nos. 4,305,872 and 4,316,891, the teachings of which are incorporated herein. These methods can be used to synthesize peptides having identity with the native PR-39 peptide amino acid sequence described herein, or to construct desired substitutions or additions of specific amino acids, which can be screened for content and evaluated for activity. PR-39 can also be commercially obtained from Magainin, Inc. (Plymouth Meeting, Pa.).

Pharmaceutical Formats

After synthesis or purchase, the PR-39 peptides (as a family of homologs and analogs with substituted amino acid residues) can be introduced as a peptide-containing preparation in a pharmaceutically acceptable format.

The PR-39 can be administered and introduced in-vivo systemically, topically, or locally. The peptide can be administered as the peptide or as a pharmaceutically acceptable acid- or base-addition salt, formed by reaction with an inorganic acid (such as hydrochloric acid, hydrobromic acid, perchloric acid, nitric acid, thiocyanic acid, sulfuric acid, and phosphoric acid); or with an organic acid (such as formic acid, acetic acid, propionic acid, glycolic acid, lactic acid, pyruvic acid, oxalic acid, malonic acid, succinic acid, maleic acid, and fumaric acid); or by reaction with an inorganic base (such as sodium hydroxide, ammonium hydroxide, potassium hydroxide); or with an organic base (such as mono-, di-, trialkyl and aryl amines and substituted ethanolamines).

PR-39 peptide and any of the PR-39 derived oligopeptide family members may also be conjugated to sugars, lipids, other polypeptides, nucleic acids and PNA; and function in-situ as a conjugate or be released locally after reaching a targeted tissue or organ. The PR-39 family of peptides may also be linked to targeting compounds for attachment in-situ to a specific cell type, tissue or organ.

V. Means for Introduction of PR-39 Peptide and/or its Shorter-Length Derived Homologs DNA Fragments and Expression Vectors A variety of means and methods are conventionally known and presently available to the user or practitioner of the present invention in order to introduce PR-39 peptide (or a derived oligopeptide family member) to living cells and tissues. One desirable means uses a prepared DNA sequence fragment encoding the PR-39 peptide (or a shorter-length homolog) in a suitable vector as the means of introduction to the intended target in-situ. These means for delivery envision and include in-vivo use circumstances; ex-vivo specimens and conditions; and in-vitro cultures. In addition, the present invention intends and expects that the prepared DNA sequence fragment coding for PR-39 peptide (or shorter-length homologs) has been inserted in a suitable expression vector and will be used in a route of administration for delivery to living tissues comprising endothelial cells, and typically vascular endothelial cells which constitute the basal layer of cells within capillaries and blood vessels generally. Clearly, the cell recipients themselves are thus eukarytoic in origin, typically mammalian cells from human and animal sources; and most typically would include the higher orders of mammals such as humans and domesticated mammalian animals kept as pets or sources of food intended for future consumption. Accordingly, the range of animals includes all domesticated varieties involved in nutrition including cattle, sheep, pigs and the like; as well as those animals typically used as pets or raised for commercial purposes including horses, dogs, cats, and other living mammals typically living with and around humans.

Clearly, the expression vectors must be suitable for transfection of endothelial cells in living tissues of mammalian origin and thus be compatible with that type and condition of cells under both in-vivo and/or in-vitro conditions. The expression vectors thus typically include plasmids and viruses as expression vectors.

Also, both the plasmid based vectors and the viral expression vectors constitute conventionally known means and methods of introduction which are conventionally recognized today as "gene therapy" modes of delivery. However, this overall approach is not the only means and method of delivery available for the present invention.

Direct Introduction of Previously Synthesized PR-39 Peptides or a PR-39 Derived Oligopeptide Family Member PR-39 peptide or an oligopeptide family member can be introduced directly as a synthesized compound to living cells and tissues via a range of different delivery means. These include the following.

1. Intracoronary delivery is accomplished using catheter-based deliveries of synthesized PR-39 peptide (or homolog member) suspended in a suitable buffer (such as saline) which can be injected locally (i.e., by injecting into the myocardium through the vessel wall) in the coronary artery using a suitable local delivery catheter such as a 10 mm InfusaSleeve catheter (Local Med, Palo Alto, Calif.) loaded over a 3.0 mm×20 mm angioplasty balloon, delivered over a 0.014 inch angioplasty guidewire. Delivery is typically accomplished by first inflating the angioplasty balloon to 30 psi, and then delivering the protein through the local delivery catheter at 80 psi over 30 seconds (this can be modified to suit the delivery catheter).

2. Intracoronary bolus infusion of PR-39 peptide (or a short-length homolog) synthesized previously can be accomplished by a manual injection of the substance through an Ultrafuse-X dual lumen catheter (SciMed, Minneapolis, Minn.) or another suitable device into proximal orifices of coronary arteries over 10 minutes.

3. Pericardial delivery of synthesized PR-39 peptide (or a shorter-length homolog) is typically accomplished by instillation of the peptide-containing solution into the pericardial sac. The pericardium is accessed via a right atrial puncture, transthoracic puncture or via a direct surgical approach. Once the access is established, the peptide material is infused into the pericardial cavity and the catheter is withdrawn. Alternatively, the delivery is accomplished via the aid of slow-release polymers such as heparin-alginate or ethylene vinyl acetate (EVAc). In both cases, once the PR-39 peptide (or homolog) is integrated into the polymer, the desired amount of PR-39/polymer is inserted under the epicardial fat or secured to the myocardial surface using, for example, sutures. In addition, the PR-39/polymer can be positioned along the adventitial surface of coronary vessels.

4. Intramyocardial delivery of synthesized PR-39 peptide (or a shorter-length homolog) can be accomplished either under direct vision following thoracotomy or using thoracoscope or via a catheter. In either case, the peptide containing solution is injected using a syringe or other suitable device directly into the myocardium. Up to 2 cc of volume can be injected into any given spot and multiple locations (up to 30 injections) can be done in each patient. Catheter-based injections are carried out under fluoroscopic, ultrasound or Biosense NOGA guidance. In all cases after catheter introduction into the left ventricle the desired area of the myocardium is injected using a catheter that allows for controlled local delivery of the material.

Pharmaceutical Carriers of PR-39 Peptides or a PR-39 Derived Oligopeptide Family Member A range of suitable pharmaceutical carriers and vehicles are known conventionally to those skilled in the art. Thus, for parenteral administration, the compound will typically be dissolved or suspended in sterile water or saline.

For enteral administration, the PR-39 peptide or homologous oligopeptide of choice will be typically incorporated into an inert carrier in tablet, liquid, or capsular form. Some suitable carriers are starches and sugars; and often include lubricants, flavorings, binders, and other materials desirable in tablet making procedures.

The PR-39 peptide and oligopeptide family of compounds can also be administered topically by application of a solution, cream, gel, or polymeric material (for example, a Pluronic™, BASF).

As an alternative, the chosen peptide can be administered in liposomes or microspheres (or microparticles), which can be injected for local or systemic delivery. Methods for preparing liposomes and microspheres for administration to a patient are conventionally known to those skilled in the art. For example, U.S. Pat. No. 4,789,734 describes methods for encapsulating biological materials in liposomes. Essentially, the material is dissolved in an aqueous solution, the appropriate phospholipids and lipids added, along with surfactants if required, and the material dialyzed or sonicated, as necessary. See also, G. Gregoriadis, Chapter 14, "Liposomes", *Drug Carriers in Biology and Medicine*, chap. 14, pp. 287–341 (1979). Microspheres formed of polymers or proteins are well known to those skilled in the art, and can be tailored for passage through the gastrointestinal tract directly into the bloodstream. Alternatively, the compound can be incorporated and the microspheres, or composite of microspheres, implanted from days to months. See, for example, U.S. Pat. Nos. 4,906,474; 4,925,673; and 3,625,214.

Examplary Introductions and Preferred Routes of Administration

A variety of approaches, routes of administration, and delivery methods have been identified herein and are available for introduction of PR-39 peptide and the derived family of oligopeptides. It is envisioned, however, that a majority of the approaches and routes of administration described herein will be medical applications and specific clinical approaches intended for use with individual human patients having specified medical problems and diagnosed pathologies. It is expected, accordingly, that the reader is familiar generally with the typical clinical human problem, pathology, and medical conditions described herein; and therefore will be able to follow and easily understand the nature of the intervention clinically using the present invention and the intended outcome and result of the clinical treatment—particularly as pertains to the stimulation of angiogenesis under in-vivo treatment conditions. A representative listing of preferred clinical approaches is given by Table 5 below.

TABLE 5

Preferred Routes of Administration

Catheter-based (intracoronary) injections and infusions;
Direct myocardial injection (intramyocardial guided);
Direct myocardial injection
(direct vision-epicardial-open chest or under thorascope guidance);
Local intravascular delivery;
Local transvascular delivery;
Perivascular delivery;
Liposome-based delivery;
Delivery in association with receptor-specific peptides;
Oral delivery;
In instances of peripheral vascular disease:
intramuscular injection,
intraarterial injection and/or infusion,
perivascular delivery with or without sustained-release polymer.

VI. Illustrative Applications for the Methodology a. Inhibition of ischemia-reperfusion injury. Restoration of blood flow to the myocardium in the setting of acute myocardial infarction leads to further damage to ischemic but still live heart muscle due to an influx of inflammatory blood cells that is mediated by NFκB-activated expression of endothelial adhesion molecules ICAM-1 and VCAM-1. Infusion of PR39 prior to restoration of flow blocks this effect due to inhibition of NFκB activity and effectively protects from further myocardial injury. Data in mice show that infusion of PR39 reduces infarct size by 60% by this mechanism.

b. Inhibition of chemical pancreatitis. Tissue injury in the pancreas due to chemical or hormonal injury is one of the more common causes of acute pancreatitis. This is largely mediated by NFκB. Pre-treatment with PR39 blocks this injury.

c. PR39 will block any other injury activated NFκB-dependent gene transcription and thus can be used to block the development of skin wounds, ulcers (stomach, duodenum), etc.

VII. Experiments and Empirical Data

To demonstrate the merits and value of the present invention, a series of planned experiments and empirical data are presented below. It will be expressly understood, however, that the experiments described and the results provided are merely the best evidence of the subject matter as a whole which is the invention; and that the empirical data, while limited in content, is only illustrative of the scope of the invention envisioned and claimed.

Experimental Series

Methods and Materials:

Cell Culture Studies

EVC304 cells (ATCC) were cultured in M199 medium supplemented with 10% fetal bovine serum (FBS) and 10 µg/ml penicillin/streptomycin. U937 cells (courtesy Dr. J. Chang, BIDMC, Boston) were cultured in RPM1640 medium supplemented with 10% FBS and 100 µg/ml penicillin/streptomycin.

Yeast Two-hybrid Screening

Two-hybrid screening was done using Clontech MATCH-MAKER GAL4 System 2 (Clontech). cDNA of porcine PR39 peptide corresponding to the 4th exon (amino acids 131 to 169) was subcloned into pAS2-1 vector as bait. Mouse embryo 3T3 MATCHMAKER cDNA library (Clontech) was screened in the yeast Y190 strain. Plasmids from HIS3/LacZ positive clones were sequenced and co-transformed with bait plasmid back into the Y190 strain to confirm the interaction.

IκBα Ubiquitination Studies

In Vitro Assay:

IκBα and its phosphorylation situes mutants $^{32}S \rightarrow ^{32}A$ and $^{36}S \rightarrow ^{36}A$ (S32A-IκBα and S36A-IκBα) in pBluscript plasmids were generously provided by T. Maniatis (Harvard University). Plasmid for the overproduction of GST-Ub (pGES-2TK-Ub) was a gift of J. Huibregtse. GST-Ub was prepared as described in Scheffner et al., Cell 75: 495–505 (1993).

Preparation of HeLa Cell Extract:

HeLa cells were harvested by centrifugation at 4,000 rpm. The packed cell volume was estimated, and the cells osmotically lysed by the addition of 5 volumes of hypotonic buffer (10 mM Tris-Cl, pH 7.9, 1.5 mM $MgCl_2$, 10 mM KCl, 0.2 mM PMSF, 0.5 mM DTT). The mixture was incubated on ice for 10 minutes, then homogenized with 12 strokes of a Dounce homogenizer (B Type pestle), The crude lysate was centrifuged for 15 minutes at 4,000 rpm, followed by recentrifugation of the supernatant at 100,000×g for 30 minutes. This supernatant was concentrated by the addition of solid $(NH_4)_2SO_4$ to 80% saturation, stirred at 4° C. for 30 minutes and centrifuged for 15 minutes at 12,000 rpm. The precipitate was resuspended in ⅕ volume of 20 mM Tris-Cl pH7.6, 20 mM KCl, 5 mM MgCl 2, 1 mM DTT, 0.5 mM PMSF, 5 µM Chymostatin and 20 µM E64, and dialyzed against >500 volumes of 20 mM Tris-Cl pH 7.6, 20 mM KCl, 5 mM MgCl2, 1 mM DTT, 10% glycerol at 4° C. overnight and stored at −70° C. until use.

Ubiquitination Assay:

$^{35}$S-IκBα and $^{35}$S-S32A/S36 IκBα were prepared by coupled in vitro transcription/translation in wheat germ extract (Promega, Madison, Wis.) using Trans$^{35}$S-Label (ICN Radiochemicals, Costa Mesa, Calif.) according to manufacturer's instructions. $^{35}$S-IκBα and $^{35}$S-S32A/S36A IκBα were removed from unincorporated radioactivity by gel filtration using a NICK-Spin column (Pharmacia Biotech, Piscataway, N.J.). $^{35}$S-IκBα or $^{35}$S-S32A/S36A IκBα (~40,000 cpm) were added to a 20 μl reaction containing 2 mM ATP, 10 mM creatine phosphate, 0.2 mg/ml creatine kinase, 70 μM GST-ubiquitin, 3.3 μM okadaic acid (Sigma, St. Louis, Mo.), 30 μm MG132, 2 μM ubiquitin aldehyde, 200 μM bestatin, 10 uM E64, 0.5 mM PMSF, and 80 μg HeLa cell extract in 20 mM Tris-Cl pH 7.6, 20 mM KCl, 10 mM $MgCl_2$, 1 mM DTT, 10% glycerol. PR-39 or control peptides were also added to individual reactions. The samples were incubated at 37° C. for 90 minutes followed by the addition Laemelli sample buffer to stop the conjugation reactions. The samples were then heated for 5 minutes at 95° C. and analyzed by SDA-PAGE on 4–15% acrylamide gradient gels (BioRad, Hurcules, Calif.). After electrophoresis, the gels were incubated with gentle stirring in 30% methanol 10% acetic acid, dried and analyzed using a Fuji phosphorimager.

Cell Culture Assay:

ECV304 cells were stably transfected with a HA-tagged ubiquitin plasmid MT123 (kind gift of Dr. G. Walz, BIDMC). The clone with the highest expression of HA-ubiquitin was treated with 10 μM PR39 for 45 min followed by treatment with 1 ng/ml TNFα for 20 min. At that point, the cells were washed and lysed and IκBα was immunoprecipitated. Following SDS-PAGE and membrane transfer of the immunoprecipitated material, the HA-ubiquitinated IκBα was visualized by Western blotting with an anti-HA antibody (Santa Cruz).

Electrophoretic Mobility Shift Assay

Nuclear extracts were prepared as described in Dyer, R. B. and N. K. Herzog, *Biotechniques* 19: 192–195 (1995). In brief, pancreatic tissue was homogenized in ice cold 0.3M sucrose, cells were subjected to iso-osmolar lysis in buffer containing NP-40 and the isolated nuclei. Nuclear protein were extracted from intact nuclei in a buffer containing 0.4 M KCl and stored in −70° C. before analysis.

Aliquots of 7.5–10 μg of nuclear protein wer mixed in 25 μl reactions containing 5 mM Tris pH 7.5, 100 mM NaCl, 1 mM DDT, 1 mM EDTA, 4% (v/v) glycerol, 0.08 mg/ml salmon sperm DNA and $H_2O$. The oligonucleotide probe (5'-AGT TGA GGG GAC TTT CCC AGG C-3', Promega, Madison, Wis.) containing the kB binding motif was end labeled with [γ-$^{32}$P] ATP using $T_4$ polynucleotide kinase. $1\times10^6$ cpm of the probe was added to the mixture, and the binding reaction was allowed to proceed for 20 min at room temperature. The unlabeled oligonucleotide was used in the specific competition assay. DNA-protein complexes were resolved in a 6% non-denaturating polyacrylamide gel in a TBE buffer at 150V. Gels were dried and exposed to Kodak Bio Max MR film at −70° C.

Experiment 1

To identify possible intracellular targets of PR-39 peptide action, a yeast two-hybrid screen of mouse cDNA library was performed using the unique 4th exon DNA sequence of porcine PR-39 gene as "bait". Four clones growing on selective media and demonstrating lacZ staining were purified and sequenced. All four clones encoded overlapping identical cDNA sequences which are highly homologous to the sequence of the human α7 (HC8) subunit of the 20S proteasome (GeneBank accession AF055983). The results are shown by FIG. 1 and reveals a PR-39/proteasome interaction and the consequential effect on IκBα degradation and NFκB activity.

FIG. 1A shows the binding of PR-39 to α7 and its fragments in the yeast two-hybrid assay. Deletion mutants of the mouse α7 subunit were cloned into yeast two-hybrid vector, and the extent of growth of lacZ+ colonies on selective medium following co-transformation with PR-39 construct in the yeast CG1945 was determined. Note that only the full length a7 construct was able to bind to PR-39. Deletion analysis showed that the presence of both the C-terminal as well as the N-terminal sequences of α7 are required for PR-39 peptide binding.

In order to confirm that PR-39 and the a7 subunit interact in cells, a polyclonal anti-PR-39 antibody was used to immunoprecipitate PR-39 protein from EVC304 cells transfected with cDNA constructs corresponding either to the full length (EVC-PR-39) or exon 4 (39 amino acid C-terminal domain) (ECV-E4) of the porcine PR-39 gene.

FIG. 1B shows the co-immunoprecipitation of PR-39 and 20S subunits in ECV cells. Full-length porcine cDNA (containing the leader sequence) and a cDNA construct corresponding to the 4th exon of porcine PR-39 gene were cloned into eukaryotic expression vector pGRE5-2 (USB) and used to stably transfect an immortalized human endothelial cell line (ECV304, ATCC). For co-immunoprecipitation, wild type ECV, full-length PR-39 (ECV-PR-39) and exon 4 PR-39 (ECV-E4) transfected cells were cultured in 10% FBS-M199. Cells were lysed with the RIPA buffer, and equal amounts of total protein were pre-cleared with non-immune rabbit serum and protein G plus/protein A-agarose beads (Calbiochem). The cleared samples were incubated at 4° C. overnight with 20 μl of polyclonal anti-PR-39 antibody and 40 μl of protein G plus/protein A-agarose beads or with the beads alone. The beads were then washed three times with PBS, resuspended in Laemmli sample buffer (2% SDS, 10% glycerol, 0.5% β-mercaptoethanol, 0.004% bromphenol blue, 50 mM Tris-HCl pH 6.8), resolved on 10% SDA-PAGE and transferred to PVDF membrane and blotted with 1:1000 mouse monoclonal anti-α7 or anti-α2 antibodies (Affiniti Research Products Ltd., UK). As a control, the total cell lysate of ECV cells was subjected to SDS-PAGE and immunoblotting with anti-α7 mAb (last lane).

FIG. 1B also shows the presence of the α7 and α2 subunits in the immunoprecipitate from ECV-PR-39 and ECV-E4 but not ECV cells as well as the presence of additional bands likely corresponding to other 20S proteasome subunits. Western blot analysis of the material immunoprecipitate from the whole cell lysate with the anti-α7 subunit monoclonal antibody demonstrated the presence of a 29 kD band corresponding to the known size of the α7 proteasome subunit in the ECV-PR-39 and ECV-E4, but not wild type ECV-304 cells.

In addition, evidence was obtained for the potential presence of other 20S proteasome subunits (FIG. 1B). Western blotting with a monoclonal antibody directed against the α2 subunit of the 20S proteasome demonstrated its presence in the anti-PR-39 antibody immunoprecipitate from the PR-39-expressing but not wild type ECV304 cells (FIG. 1B). Taken together, these results demonstrate that PR-39 can bind to the 20S proteasome particle via an interaction with the a7 subunit.

Since such an interaction with a proteasome subunit may result in inhibition of proteasome-mediated protein degradation, the effect of PR-39 expression on the degradation of IκBα, an important regulator of gene transcription, was assessed. Stable expression of PR-39 constructs in ECV304 cells resulted in increased levels of IκBα.

FIG. 1C shows the stable expression of PR-39 increases IκBα expression in ECV304 cells. For IκBα expression studies, normally proliferating wild type ECV304 cells (ECV) or ECV-PR-39 and ECV-E4 cells were lysed in the loading buffer, subjected to electrophoresis on 10% SDS-PAGE gel and transferred to a PVDF membrane. IκBα expression was then determined by Western blotting with anti-IκBα antibody (Santa Cruz, Inc.). ECV304 cells treated for 2 hr with 10 μM of lactacystin (LC) were used as control. Note increased IκBα levels in ECV-E4 and ECV-PR-39 cells as well as in lactacystin-treated cells.

FIG. 1D shows the dose-dependent effect of PR-39 treatment on IκBα protein levels. Western blotting of ECV cell lysate was carried out following 2 hr exposure to buffer (0) or 100 or 50 nM of PR-39. Note the dose-dependent increase in IκBα protein levels. Clearly, exposure of wild type ECV304 cells to the synthetic PR-39 peptide led to a dose-dependent increase in IκBα levels.

Tumor necrosis factor (TNF)-α is known to induce rapid degradation of IκBα by the Ub-proteasome pathway. To test whether PR-39 can inhibit TNF-α induced degradation of IκBα, a human monocytic cell line U937 was employed that normally exhibits significant baseline levels of IκBα.

As shown by FIG. 1E, PR-39 prevents TNF-a induced degradation of IκBα. U937 cells were cultured in 10% FBs-RPMI medium in the absence (−) or presence of TNF-a (1 ng/ml). 10 min following TNF-α addition, the cells were washed and IκBα protein levels assessed by Western blotting.

The results show TNF-α caused a rapid decline of the level of IκBα in these cells, and this effect was markedly reduced by pretreatment with PR-39 or proteasome inhibitos lactacystin or MG132 (FIG. 1E). Note that a complete disappearance of IκBα occurs in TNF-α treated cells with 45 min of pretreatment with 100 nM of PR-39 or 10 μM of MG132 or lactacystin (LC) prior to addition of blocked TNF-α, blocked cytokine-induced degradation of IκBα expression.

To test whether treatment with PR-39 peptide irreversibly blocked IκBα degradation, U937 cells were pretreated with the peptide and then were extensively washed, and 45 min later exposed to TNF-α. In parallel cells were exposed to MG132, a rapidly reversible competitive inhibitor of the proteasome or with lactacystin which covalently and irreversibly modifies the active site threonine residues. The results are shown by FIG. 1F.

FIG. 1F demonstrates the reversibility of PR-39 inhibition of IκBα degradation. U937 cells were pretreated with 100 nM of PR-39, 10 μM of either MG132 or lactacystin (LC) or buffer (Control) for 45 min. These cells were then extensively washed with fresh medium. 45 min later TNF-α (1 ng/ml) was added to medium, and the extent of IκBα degradation was determined 10 min later by Western blotting. Such Western blot analysis demonstrated the complete disappearance of IκBα protein in PR-39 and MG132-treated cells while pretreatment with lactacystin irreversibly blocked proteasome-mediated degradation of IκBα.

Experiment 2

To show that the PR-39 peptide not only prevented inhibition of IκBα degradation but also inhibited NFκB-dependent transcription in cell culture and in mice (i.e., that the IκBα protein was functional), ECV304 cells were transiently transfected with a reporter construct containing a tandem of four NFκB binding sites in front of a minimal TK promoter driving luciferase cDNA. The results are presented by FIG. 2A.

Figure 2:
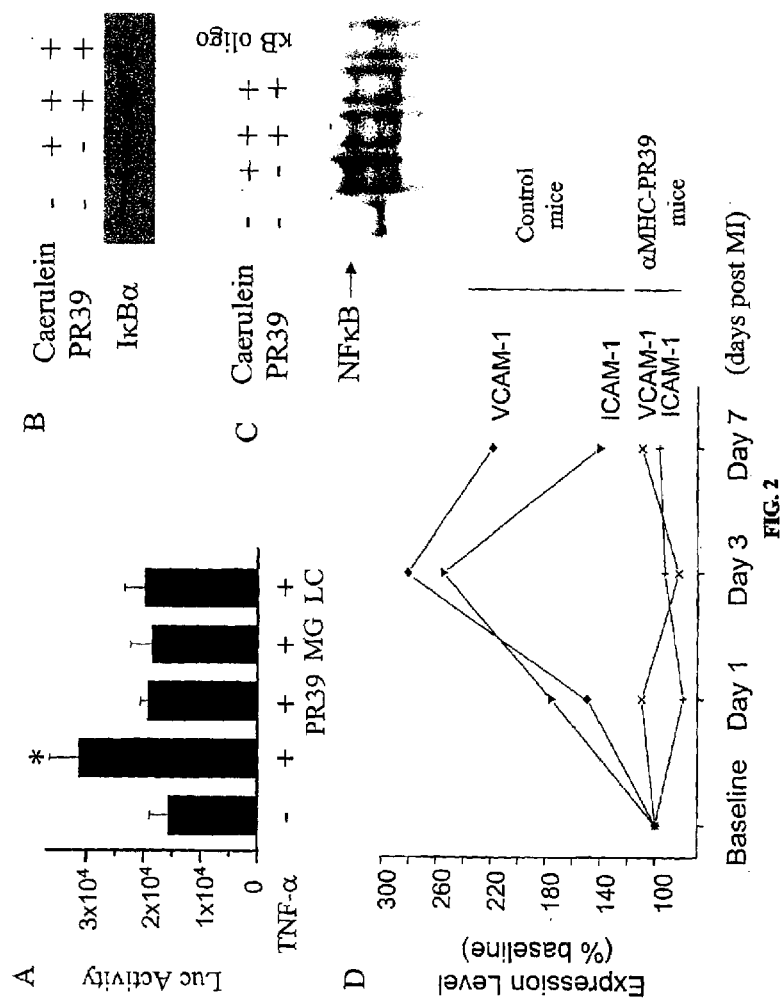
FIGS. 2A–2D are presentations of empirical data showing the effect of PR-39 peptide upon inhibition of NFκB-dependent gene expression in cell culture and mice.

FIG. 2A shows that PR-39 administration blocks NFκB-dependent gene expression in cell culture. The effect of PR-39-mediated inhibition of IκBα degradation on NFκB-dependent transcription was tested in ECV304 cells transiently transfected with pNFκB-Luc reporter vector. Exposure to 1 ng/ml TNF-α led to a significant increase in luciferase activity that was completely blocked by 45 min of pretreatment with 10 nM of PR-39 or 10 μM of either MG132 (MG) or lactacystin (LC)*p<0.01 vs. control (luciferase activity in the absence of TNF-α).

To study whether PR-39 can also inhibit NFκB activation in intact animals, two mouse models of acute injury were used—acute pancreatitis and acute myocardial infarction. The results are shown by FIGS. 2B and 2C respectively.

FIG. 2B demonstrates that PR-39 blocks IκBα degradation in mouse pancreas following induction of acute pancreatitis. Male mice weighing 20–25 g (ICR, Charles River Laboratories, Wilmington, Mass.) were pretreated with PR-39 (10 mg/kg, i.v.) or physiological saline 1 hour before injecting 50 μg/kg i.v. of caerulein (Research Plus, Bayonne, N.J.) to induce acute pancreatitis. 30 min later the animals were sacrificed in a $CO_2$ chamber and a 75–100 mg piece of pancreas was removed for Western blotting and NFκB gel shift assays. Note preservation of IκBα in both PR-39-treated animals.

FIG. 8C shows NFκB-dependent transcription in the mouse pancreas. NFκB activation in mouse pancreatic tissues in the setting of caerulein-induced pancreatitis was examined using electromobility shift assay. Note almost complete disappearance of NFκB gel shift in PR-39 treated animals. 100× excess of oligonucleotide competitor of NFκB binding site was used to demonstrate band specificity (κB oligo).

As empirically shown, induction of acute pancreatitis by treatment with the cholecystokinin analog caerulein leads to the prompt disappearance of IκBα (FIG. 2B) and activation of NFκB-dependent transcription in the pancreas (FIG. 8C). Intravenous injection of 10 mg/kg of PR-39 one hour prior to caerulein administration largely prevented IκBα degradation and, consequently, NFκB-dependent gene expression as assessed by DNA gel shifts.

NFκB-dependent transcription is also activated following induction of ischemia in the heart, leading to increased expression of several adhesion molecules, including ICAM-1 and VCAM-1. To test the effect of PR-39 peptide on NFκB-dependent gene expression in this model, we assessed VCAM-1 and ICAM-1 protein levels following induction of myocardial infarction in transgenic mice expressing PR-39 cDNA in cardiac myocytes (αMHC-PR-39) and age-matched control mice. The result is given by FIG. 2D.

FIG. 2D shows that PR-39 blocks NFκB-dependent gene expression in a mouse infarct model. Transgenic mice stably expressing PR-39 in cardiac myocytes (αMHC-PR-39 mice) or litter mate controls (control mice) were subjected to acute coronary artery ligation as described (30) and randomized to intraperitoneal implantation of Alzet minipumps (Alza Corp, Palo Alto, Calif.) delivering 1 μg/kg/24 hr of PR-39 or buffer. Myocardial tissues collected 1, 3 or 7 days later were subjected to Western blot analysis for ICAM-1 and VCAM-1 gene expression that were normalized to expression levels prior to induction of infarction. Note the rapid increase in both ICAM-1 and VCAM-1 expression in control but not αMHC-PR-39 mice.

The levels of both proteins increased significantly following myocardial infarction in control mice by 24 hr, reaching a peak by 72 hr and then gradually declined. In contrast, induction of myocardial infarction had no effect on either ICAA-1 or VCAM-1 protein levels in αMHC-PR-39 mice.

Experiment 3

One possible explanation of the PR-39-dependent inhibition of IκBα degradation would be that the peptide like MG132 reversibly inhibits all proteasome function, thus generally suppressing intracellular protein degradation. Therefore the extent of degradation of long-lived cell proteins before or following exposure was compared to either PR-39 or MG132. The result is given by FIG. 3A.

Figure 3:
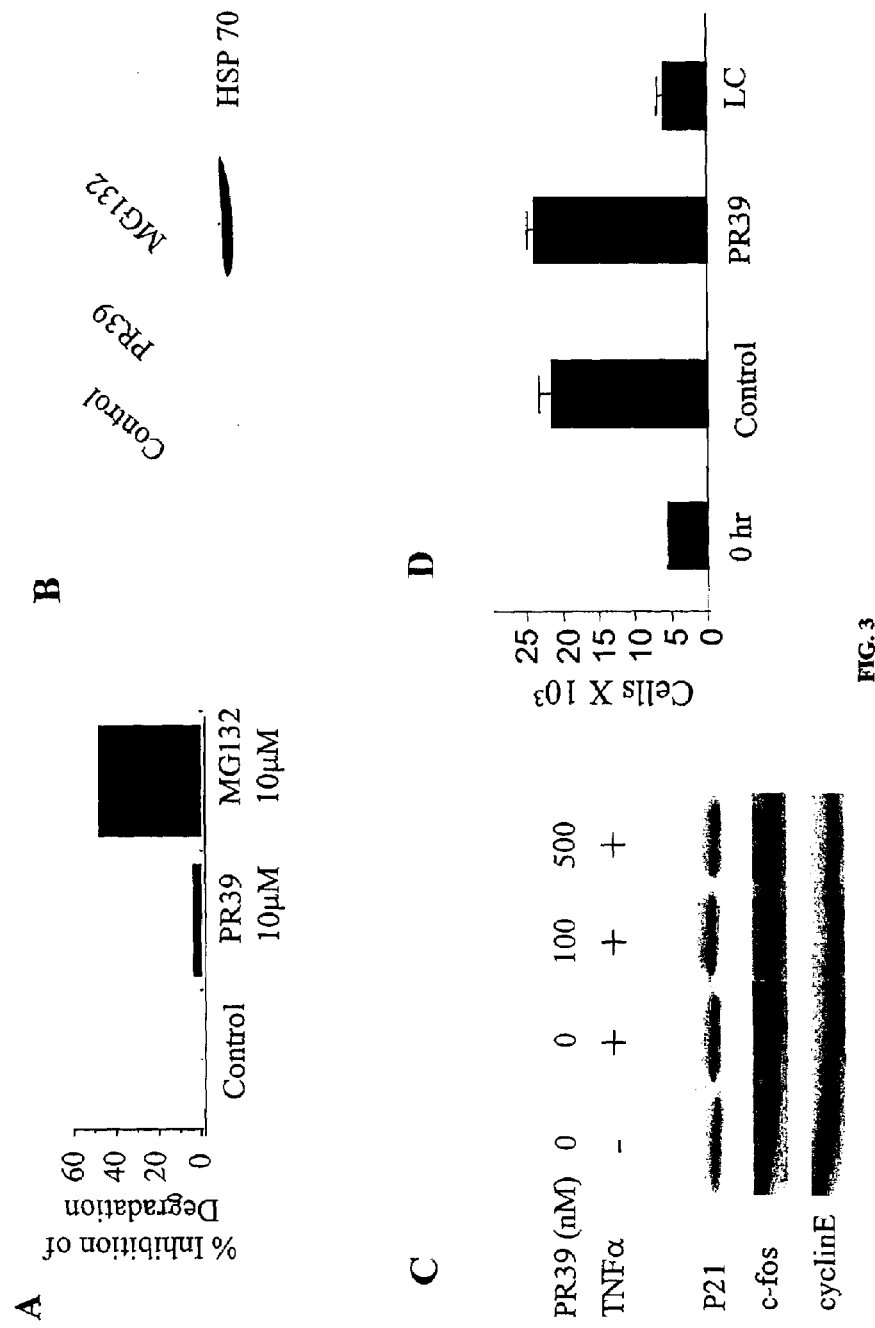
FIGS. 3A–3D are presentations of empirical data showing the selective nature of the PR-39 peptide effects.

FIG. 3A shows that PR-39 does not substantially affect proteasome-dependent degradation of total cellular proteins. Exponentially proliferating U937 cells were grown in 10% FBS-RPMI 1640 methionine-free medium supplemented with 200 μCi $^{35}$S Met for 16 hr. Cells were then washed with complete RPMI 1640 medium 3 times and cultured in 10% FBS-RPMI (chase) in the presence of 10 μM of either PR-39 or MG132 or an equal volume of PBS. Chloroquin (45 μM) was added to all cultures to prevent the lysosomal protein degradation. 1 hr later the cells were lysed, and TCA soluble $^{35}$S counts were measured in a liquid scintillation counter (LKB). All experiments were carried out in triplicate and repeated three times. The data are shown as mean±standard deviation.

Note significantly lower inhibition of total cell protein degradation by PR-39 than by MG132 in FIG. 3A. After 16 hr metabolic labeling of total cell protein in ECV304 cells, MG132 treatment resulted in approximately 50% inhibition of total cell protein degradation, in accordance with previously reported results. In contrast, administration of PR-39 had little or no effect on this process.

To confirm that PR-39 does not cause a general inhibition of protein degradation, the expression level of HSP70, a major heat shock protein whose expression is stimulated by proteasome inhibitors, was studied. FIG. 3B shows the lack of induction of HSP70 expression in PR-39-treated cells. Western blotting of cell extract from untreated (control) and PR-39-(1μM) or MG132-(1 μM) treated U937 cells demonstrated the appearance of HSP70 expression after 3 hr exposure to MG132 but not PR-39. Western blot analysis demonstrated a striking increase in HSP70 levels in cultured ECV304 cells following treatment with 10 μM of MG132. However, exposure to a similar concentration of PR-39 failed to stimulate HSP70 accumulation.

In addition, studies in ECV304 cells with specific antibodies failed to demonstrate any effect of PR-39 treatment on the levels of several proteins principally controlled by proteasome-dependent degradation including the cell cycle inhibitor p21 and cyclin E and transcription factor c-fos. This is shown by FIG. 3C.

Note that FIG. 3C shows the effect of PR-39 administration on proteasome-dependent protein levels in U937 cells. The level of proteasome-regulated cell cycle repressor p21, cyclin E and c-fos proteins were determined by Western blotting in U937 cells pretreated with various amounts of PR-39 and then exposed to TNF-α (1 ng/ml). The lack of PR-39 dependent inhibition of proteasome-mediated degradation of these proteins is demonstrated.

Prolonged exposure to proteasome inhibitors tend to induce apoptosis in cell culture. To assess the potential cytotoxicity of PR-39, ECV304 cells were cultured in the presence of 10 μM of PR-39, MG132 or lactacystin.

FIG. 3D shows that PR-39 does not affect cell growth in culture. 50,000 ECV304 cells were plated in 6 well plates in 10% FBS-M199 and synchronized by serum deprivation in 0.5% FBS-DMEM for 48 hr. At the end of that time, cell culture medium was changed to 10% FBS-M199 and 10 μM of PR-39, lactacystin or buffer (control) were added. Forty eight hours later cell counts were determined using a Coulter Counter (Coulter Instruments, Inc.). All experiments were performed in triplicate and repeated 2 times (mean±SD). Note the markedly decreased cell count in lactacystin-treated culture and the lack of significant growth inhibition by PR-39 revealed by FIG. 3D.

Moreover, the cell counts (48 hrs) documented that, while addition of PR-39 did not affect the cells' ability to proliferate, exposure of these cells to either MG132 or lactacystin led to a significant decline in cell counts. These results demonstrate that PR-39 peptide is able to inhibit IκBα degradation without significantly affecting overall protein degradation in cells.

Experiment 4

The preceding experiments suggest that PR-39 peptide inhibits IκBα degradation in a selective manner. To explore potential mechanisms of this selective inhibition, the effect of peptide administration on IκBα phosphorylation and ubiquitination was studied. It is known that TNF-α treatment leads to phosphorylation of IκBα, which is required for its subsequent ubiquitination. The result is indicated by FIG. 4A.

Figure 4:
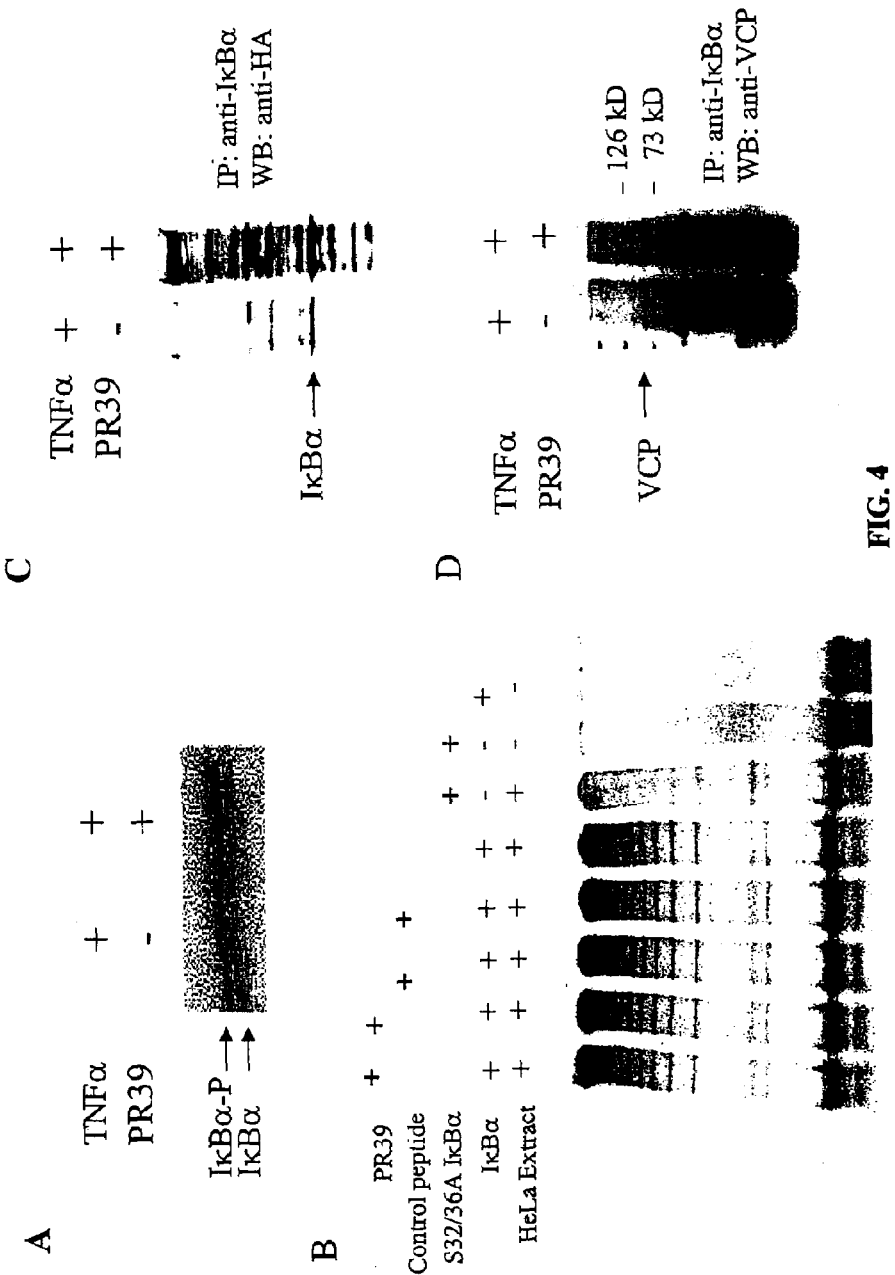
FIGS. 4A–4D are presentations of empirical data showing that PR-39 peptide administration does not affect IκBα phosphorylation or ubiquitination.
Figure 6:
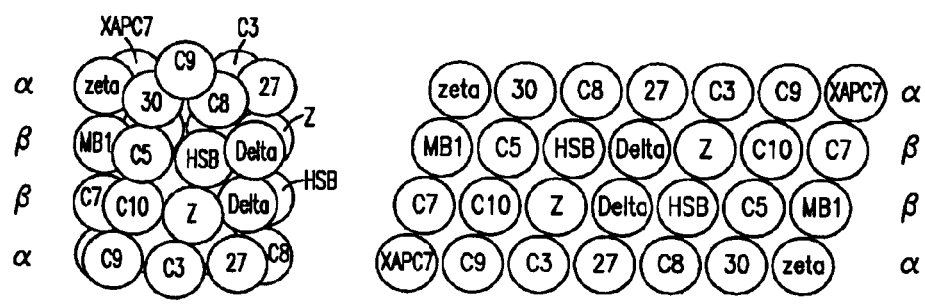

FIG. 4A shows the effect of PR-39 on IκBα phosphorylation in cell culture. U937 cells cultured in the absence (−) or presence (+) of pretreatment with 10 μM PR-39 were exposed to 1 ng/ml TNFα. 45 min later the cells were lysed and subjected to SDS-PAGE and Western blotting with anti-IκBα antibody. Note the increased amount of the typical-appearing phosphorylated IκBα band in PR-39 treated cells.

Western blotting of U937 cell lysates after in vivo $^{32}$P labeling demonstrated the appearance of the phosphorylated form of IκBα following TNF-α exposure. Pretreatment with PR-39 increased the amount of the phosphorylated form of IκBα presumably due to inhibition of its degradation.

To test the effect of PR-39 on IκBα ubiquitination in a cell free system, HeLa cell extract was used to ubiquitinate in vitro transcribed, translated and phosphorylated IκBa. FIG. 4B shows the effect of PR-39 on IκBα ubiquitination in vitro. In vitro ubiquitination of phosphorylated IκBα protein was carried out using crude HeLa cell extract in the presence of a control peptides (lanes 1 and 2), PR-39 peptide (lanes 3 and 4) or in the absence of both (lane 5). Note that the addition of either PR-39 peptide at two different concentrations or of a control (random) peptide failed to affect IκBα ubiquitination. At the same time, no ubiquitination of phosphorylation site IκBα mutants (lanes 6 and 7) or unphosphorylated IκBα (wt IκBa, lane 8) was detected.

Clearly, therefore, in the absence of PR-39 incubation of phosphorylated IκBα protein with a HeLa extract led to the appearance of multiple high molecular weight uniquitinated forms of IκBα. The addition of PR-39 peptide in an amount sufficient to inhibit IκBα degradation in cell culture had no effect on the extent of IκBα ubiquitination in this assay.

To assess the effect of PR-39 peptide treatment on IκBα ubiquitination in intact cells, a stable ECV304-derived cell line expressing HA-tagged ubiquitin was generated. FIG. 4C shows the effect of PR-39 on IκBα ubiquitination in cell culture. HA-Ub expressing ECV304 cells were exposed to 1 ng/ml TNF-α in the presence (+) or absence (−) of 10 μM PR-39 pretreatment. 45 min later the cells were lysed and subjected to IκBα immunoprecipitation followed by Western blotting of the pellet material with anti-HA antibody. Note the presence of multiple ubiquitinated IκBα intermediaries in PR-39 peptide treated cells but not in control cells.

Immunoprecipitation of IκBα followed by Western blotting with anti-HA antibody thus demonstrated the accumulation of more ubiquitinated IκBα complexes in cells pretreated with 10 μM of PR-39 than in untreated cells. These findings together argue that PR-39 does not block the ubiquitination process but does inhibit the degradation of ubiquitinated IκBα by the 26S proteasome.

A recent study [Dai et al., *J. Biol. Chem.* 273: 3562–3573 (1998)] suggested that binding of the ubiquitinated IκBα to VCP, a 26S proteasome associated protein, is necessary but not sufficient for subsequent IκBα degradation. FIG. 4D shows that PR-39 does not inhibit IκBα-VCP binding. Wild type ECV304 cells (treated as described in FIG. 4C) were subjected to immunoprecipitation with anti-IκBα antibody (IκBα-IP) followed by Western blotting with anti-VCP-3 antibody (1:3000, dilution; a kind gift of Dr. C. C. Li (NIH)). Note the presence of 90 kD VCP band in the presence or absence of PR-39 treatment.

The results of FIG. 4D reveal that Western blotting with the anti-VCP antibody demonstrated the presence of this protein in the anti-PR-39 antibody immunoprecipitate of the ECV-PR-39 cells (not shown). Western blot analysis of anti-IκBα antibody immunoprecipitated material from ECV304 cells demonstrated the presence of VCP in accord with the previously reported study. Pretreatment with PR-39 increased the amount of VCP in the IκBα immunoprecipitate (FIG. 4D) as would be expected given the increased amount of ubiquitinated forms of IκBα in the PR-39-treated cells. Accordingly, PR-39 does not interfere with IκBα-VCP binding.

Conclusions Drawn from Experimental Series

1. The empirical results presented several types of evidence that the naturally occurring anti-bacterial 39 amino acid peptide, PR-39, selectively inhibits IκBα degradation in cultured cells and in two different mice models. Stable expression of this PR-39 peptide resulted in increased IκBα content in cell culture; while pretreatment of cultured cells with the PR-39 peptide inhibited TNF-a-induced degradation of IκBα and abolished induction of NFκB-dependent transcriptional activity. Moreover, pretreatment with the PR-39 peptide blocked IκBα degradation and activation of NFκB-dependent transcription in the mouse pancreas following purposeful induction of chemical pancreatitis. Finally, transgenic expression of PR-39 peptide in mouse cardiac myocytes prevented expression of NFκB-dependent endothelial adhesion genes VCAM-1 and ICAM-1 in the clinical setting of acute myocardial ischemia.

2. While the ability to inhibit IκBα degradation in-situ may imply that PR-39 peptide acts as a proteasome inhibitor, several empirical observations clearly set it apart from all the small molecule proteasome inhibitors described to date. Most important in this regard is the selective nature of the PR-39 peptide effect. This selectivity is indicated: (a) by the lack of any effect on overall proteasome-dependent protein degradation in cells; (b) by the absence of induction of heat shock proteins such as HSP70; and (c) by the lack of toxicity following a long-term exposure in cell culture or transgenic expression in mice. In contrast, exposure of cultured cells to the proteasome inhibitors, MG132 and lactacystin, leads to a general reduction in intracellular proteolysis, a rapid increase in HSP70 expression and cell death (as reported in the scientific literature). Furthermore, known direct inhibitors of 20S proteasome affect its active sites and therefore the inhibition of proteolysis as an event is not specific to any particular protein or class of proteins.

3. Selectivity as a characteristic effect can be achieved, however, as an indirect action by blocking substrate-specific steps in the degradative pathway. Experiments were performed to determine whether the selective inhibition by PR-39 peptide of IκBα degradation is due to inhibition of known pathway steps required for its degradation, including phosphorylation, ubiquitination and VCP binding. Studies in the cell free-system failed to show any effect of PR-39 peptide treatment on ubiquitination of IκBα, while the cell culture experiments demonstrated an accumulation of phosphorylated and ubiquitinated forms of IκBα in the PR-39 peptide treated cells. Furthermore, PR-39 peptide did not interfere with the binding of ubiquitinated IκBα to VCP. These findings evidence an interaction mechanism in which PR-39, while attached to the 26S proteasome, prevents recognition or binding of the ubiquitinated IκBα-VCP complex or blocks this complex's translocation into the 26S proteasome.

4. Several contrasting experimental results described by the Experimental Series herein are also consistent with such an action of PR-39 on the 26S proteasome. The PR-39 peptide is able to bind with high affinity directly to the α7 subunit of the proteasome, as shown in the yeast two-hybrid assay as well as by co-immunoprecipitation with the anti-PR-39 antibody. Furthermore, as a result of such direct binding to α7, PR-39 peptide is able to bring down at least one other (α2) 20S subunit (and probably other subunits as well) indicating that the peptide binds to the whole 20S particle without causing its dissociation. While the precise site of interaction on the α7 subunit or on PR-39 has not yet been fully established, the high negative charge of the C-terminal end of the α7 subunit which makes it a likely site for binding of the postively charged PR-39 molecule. The α7 C-terminal sequence is actually the most negatively charged sequence of any of the proteasome a subunits; and it has the ability to assemble into heptameric ring structures by itself as well as to induce ring formation of other a subunits.

5. However, it is unclear as yet precisely how PR-39 interaction with the 26S proteasome causes the observed selective inhibition of the degradation of phosphorylated and ubiquitinated IκBα. One mode of possible mechanism would interfere with the binding of the ubiquitinated IκBα-VCP complex to the 26S proteasome. The observed inhibition of the NFκB-dependent transcription in PR-39 peptide treated cells or animals is consistent with this mechanism of action since inhibition of VCP-IκBα binding to the proteasome would leave the ubiquitinated IκBα in complex with NFκB. Alternatively, PR-39 peptide may interfere with another, yet unidentified, pathway step involved in IκBα degradation by the proteasome. Another possibility is that PR-39 binding to the α7 subunit may alter the 3-dimensional proteasome architecture or interaction of the 20S particle and the 19S regulatory subunit that would affect the entry of certain protein substrates into the 20S cylinder. All of these possible modes of action are consistent with the empirical observation that PR-39 inhibition of IκBα degradation is dose-dependent and reversible, apparently requiring the continuous presence of the PR-39 peptide.

The present invention is not to be limited in form nor restricted in scope except by the claims appended hereto.

---

SEQUENCE LISTING (1) GENERAL INFORMATION:

(iii) NUMBER OF SEQUENCES: 6

(2) INFORMATION FOR SEQ ID NO: 1:

(i) SEQUENCE CHARACTERISTICS:
      (A) LENGTH: 39 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO: 1:

```
Arg Arg Arg Pro Arg Pro Pro Tyr Leu Pro Arg Pro Arg Pro Pro Pro
1               5                   10                  15

Phe Phe Pro Pro Arg Leu Pro Pro Arg Ile Pro Pro Gly Phe Pro Pro
            20                  25                  30

Arg Phe Pro Pro Arg Phe Pro
        35
```

(2) INFORMATION FOR SEQ ID NO: 2:

(i) SEQUENCE CHARACTERISTICS:
      (A) LENGTH: 39 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO: 2:

```
Arg Arg Arg Pro Arg Pro Pro Tyr Leu Pro Arg Pro Arg Pro Pro Pro
1               5                   10                  15

Phe Phe Pro Pro Arg Leu Pro Pro Arg Ile Pro Pro Gly Phe Pro Pro
            20                  25                  30

Arg Phe Pro Pro Arg Phe Pro
        35
```

(2) INFORMATION FOR SEQ ID NO: 3:

(i) SEQUENCE CHARACTERISTICS:
      (A) LENGTH: 15 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO: 3:

```
Arg Arg Arg Pro Arg Pro Pro Tyr Leu Pro Arg Pro Arg Pro Pro
1               5                   10                  15
```

(2) INFORMATION FOR SEQ ID NO: 4:

```
        (i) SEQUENCE CHARACTERISTICS:
            (A) LENGTH: 11 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 4:

Arg Arg Arg Pro Arg Pro Pro Tyr Leu Pro Arg
1               5                   10

(2) INFORMATION FOR SEQ ID NO: 5:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 5:

Arg Arg Arg Pro Arg Pro Pro Tyr
1               5

(2) INFORMATION FOR SEQ ID NO: 6:

(i) SEQUENCE CHARACTERISTICS:
            (A) LENGTH: 39 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 6:

Arg Arg Arg Pro Arg Pro Pro Tyr Leu Pro Arg Pro Arg Pro Pro
1               5                   10                  15

Phe Phe Pro Pro Arg Leu Pro Pro Arg Ile Pro Pro Gly Phe Pro Pro
            20                  25                  30

Arg Phe Pro Pro Arg Phe Pro
            35
```

What we claim is:

1. A method for decreasing the activity of NFκB transcription factor within a targeted collection of viable cells in-situ, said method comprising the steps of:

identifying a collection of cells comprising viable cells in-situ as a target for decreased NFκB activity;

providing means for effecting an introduction of at least one member selected from the group consisting of the PR-39 oligopeptide collective to the cytoplasm of said targeted collection of cells;

introducing at least one member of the PR-39 oligopeptide collective to the cytoplasm of said targeted collection of cells using said effecting means;

allowing said introduced PR-39 oligopeptide collective member to interact with such IκBα and proteasomes as are present within the cytoplasm of said cells in said targeted collection whereby (a) at least some of the proteasomes interact with said introduced PR-39 oligopeptide collective member, (b) at least a part of the proteolytic activity mediated by said proteasomes becomes selectively altered by said interaction with said introduced PR-39 oligopeptide collective member, (c) the selectively altered proteolytic activity of said proteasomes results in a marked inhibition of IκBα degradation in-situ within the cytoplasm of said cells in said targeted collection, and (d) said reduction of IκBα degradation in-situ results in a decrease in activity for such NFκB transcription factor as is present in-situ within the cytoplasm of said cells in said targeted collection.

2. The method as recited in claim 1 wherein said collection of viable cells includes at least one type of cell selected from the group consisting of endothelial cells, myocytes and myoblasts, fibrocytes and fibroblasts, epithelial cells, osteocytes and osteoblasts, neuronal cells and glial cells, erythrocuctes, leukocytes, and progenitor cells of all types.

3. The method as recited in claim 1 wherein said collection of cells comprises at least one tissue selected from the group consisting of myocardium, skeletal muscle, smooth muscle, an artery, a vein, lung, brain, kidney, spleen, liver, gastrointestinal tissue, nerve tissue, limbs, and extremities.

4. The method as recited in claim 1 wherein said means for effecting an introduction of a PR-39 oligopeptide collective member include one selected from the group consisting of catheter-based introduction means, injection-based introduction means, infusion-based introduction means, localized intravascular introduction means, liposome-based introduction means, receptor-specific peptide introduction means, and slow releasing means for peptide secretion in living cells and sequested organisms.

5. The method as recited in claim 1 wherein said means for effecting an introduction of a PR-39 oligopeptide collective member includes the DNA sequences coding for PR-39 oligopeptides of different sizes inserted in a suitable vector for transfection and subsequent expression of peptides within said cells in said targeted collection.

6. The method as recited in claim 1 wherein said method is practiced under in-vivo conditions.

7. The method as recited in claim 1 wherein said method is practiced under in-vitro conditions.

* * * * *